US012805723B2

(12) United States Patent
Ehnholm et al.

(10) Patent No.: US 12,805,723 B2
(45) Date of Patent: Nov. 24, 2026

(54) METHOD AND APPARATUS FOR DETERMINING PHYSIOLOGICAL PARAMETER

(71) Applicant: ICARE FINLAND OY, Vantaa (FI)

(72) Inventors: Gosta Ehnholm, Helsinki (FI); Matti Raudasoja, Vantaa (FI); Viktor Honkanen, Vantaa (FI); Lauri Kangas, Vantaa (FI); Teemu Herranen, Vantaa (FI); Mika Salkola, Vantaa (FI)

(73) Assignee: ICARE FINLAND OY, Vantaa (FI)

( * ) Notice: Subject to any disclaimer, the term of this patent is extended or adjusted under 35 U.S.C. 154(b) by 344 days.

(21) Appl. No.: 18/579,699

(22) PCT Filed: Jun. 22, 2022

(86) PCT No.: PCT/FI2022/050451
§ 371 (c)(1),
(2) Date: Jan. 16, 2024

(87) PCT Pub. No.: WO2023/012402
PCT Pub. Date: Feb. 9, 2023

(65) Prior Publication Data

US 2024/0315557 A1 Sep. 26, 2024

(30) Foreign Application Priority Data

Aug. 5, 2021 (FI) ...................................... 20215838

(51) Int. Cl.
*A61B 3/16* (2006.01)
*A61B 3/00* (2006.01)
(Continued)

(52) U.S. Cl.
CPC .............. *A61B 3/16* (2013.01); *A61B 3/0025* (2013.01); *G01L 9/0094* (2013.01); *G01L 9/14* (2013.01)

(58) Field of Classification Search
CPC ........... A61B 3/16; A61B 3/0025; A61B 3/10; A61B 5/6821; G01L 9/0094; G01L 9/14
See application file for complete search history.

(56) References Cited

U.S. PATENT DOCUMENTS

| | | | |
|---|---|---|---|
| 6,093,147 | A | 7/2000 | Kontiola |
| 2008/0103381 | A1 | 5/2008 | Kontiola |

(Continued)

FOREIGN PATENT DOCUMENTS

| | | | |
|---|---|---|---|
| EP | 3581089 | A1 | 12/2019 |
| JP | 2019502451 | A | 1/2019 |

(Continued)

OTHER PUBLICATIONS

Trans-tek. "LVT—Linear Velocity Transducers." Medital, Dec. 15, 2019, web.archive.org/web/20191215190117/https://medital.com/products/lvt-linear-velocity-transducers. (Year: 2019).*

(Continued)

*Primary Examiner* — Adam J Eiseman
*Assistant Examiner* — Lucy Eppert
(74) *Attorney, Agent, or Firm* — ZIEGLER IP LAW GROUP, LLC.

(57) ABSTRACT

Disclosed is an apparatus for determining physiological parameter. The apparatus has an elongated magnetic probe, a driver coil arranged partially to surround the elongated magnetic probe, a measurement coil with at least a first section and a second section and a controller. The controller is configured to selectively energize the driver coil to create a magnetic force to initiate movement of the elongated magnetic probe to a direction of the first end, measure a first induced voltage and common induced voltage values, determine locator values as a function of time, map the locator values as a function of time from the time domain to a spatial domain and calculate from the spatial domain locator values, (Continued)

a first velocity profile of the elongated magnetic probe, and use the calculated first velocity profile of the elongated magnetic probe to determine the physiological parameter.

18 Claims, 16 Drawing Sheets

(51) Int. Cl.
*G01L 9/00* (2006.01)
*G01L 9/14* (2006.01)

(56) References Cited

U.S. PATENT DOCUMENTS

| | | | | |
|---|---|---|---|---|
| 2009/0234215 | A1 | 9/2009 | Piletskiy et al. | |
| 2016/0120697 | A1 | 5/2016 | Farley et al. | |
| 2016/0278852 | A1 | 9/2016 | Sliwa et al. | |
| 2018/0368681 | A1* | 12/2018 | Makkeli | A61B 3/16 |
| 2019/0380577 | A1 | 12/2019 | Martin et al. | |
| 2022/0409044 | A1* | 12/2022 | Salkola | A61B 3/16 |

FOREIGN PATENT DOCUMENTS

| | | | |
|---|---|---|---|
| JP | 2019213863 | A | 12/2019 |
| WO | 2010063024 | A1 | 6/2010 |
| WO | 2019234292 | A1 | 12/2019 |

OTHER PUBLICATIONS

Cimbala , John M. Linear Velocity Measurement, Nov. 19, 2013, www.me.psu.edu/cimbala/me345/Lectures/Velocity_measurement.pdf. (Year: 2013).*

NHS. Repeat Pressures Patient Information Sheet . . . , Nov. 2018, www.glosloc.co.uk/wp-content/uploads/2018/11/Repeat%20IOP%20Patient%20Infomation%20V4%20Nov%202018.pdf. (Year: 2018).*

European Patent Office, International Search Report and Written Opinion of the International Searching Authority, Application No. PCT/FI2022/050451, Mailed Sep. 9, 2022, 13 pages.

Finnish Patent and Registration Office, Search Report, Application No. 20215838, Mailed Nov. 4, 2021, 2 pages.

Japan Patent Office, Notice of Reasons for Refusal, Application No. 2024501711, mailed Dec. 1, 2025, 4 pages, English Translation, 3 pages.

* cited by examiner

| U+ | U- | 1000*(U+/U-) |
|---|---|---|
| 559.2 | 387.09 | 692.2 |
| 574.7 | 311.52 | 542.1 |
| 596.3 | 223.52 | 374.8 |
| 599.4 | 128.15 | 213.8 |
| 599.8 | -13.431 | -22.4 |
| 573.1 | -124.19 | -216.7 |
| 539.5 | -266.42 | -493.8 |
| 487.6 | -371.36 | -761.6 |

| U+ | U- | 1000*(U-/U+) |
|---|---|---|
| 622.3 | 163.3 | 242.41 |
| 616.6 | 39.2 | 63.57 |
| 606.8 | -116.8 | -192.49 |
| 587.4 | -287 | -488.59 |
| 588.5 | -436.3 | -741.38 |
| 590.6 | -514.85 | |
| 570.3 | -529.11 | |
| 532.1 | -507.34 | |

METHOD AND APPARATUS FOR DETERMINING PHYSIOLOGICAL PARAMETER

TECHNICAL FIELD

The present disclosure relates generally to ophthalmic treatment device; and more specifically, to methods and systems for determining physiological parameter.

BACKGROUND

Aqueous humor is a transparent water-like fluid produced in the eye to provide protection to the lens and maintains fluid pressure in the eye. The fluid pressure in the eye is known as intra-ocular pressure. Furthermore, the intra-ocular pressure is a physiological parameter that determines the strength of the eye, and find signs of optic nerve damage that might affect vision. Typically, the normal pressure in the eyes changes during the day and differ from person to person. However, in case the intra-ocular pressure is consistently too high or too low, there may be problems with the vision.

Traditionally, a tonometry test measures the intra-ocular pressure. Herein, the tonometry test uses a tonometer to determine the firmness of the eye. Conventionally, Goldman Applanation Tonometer (GAT) uses numbing drops to anesthetize the eyes, wherein a small amount of non-toxic dye is placed in the eye. Subsequently, a small probe gently touches the surface of the eye and the intra-ocular pressure is determined. Herein, the intra-ocular pressure is measured based on the force required to gently flatten a fixed area of the surface of the eye. However, the thickness of the eye, elasticity of the eye, and the amount of non-toxic dye used is a source of error and affects the accuracy of measurements obtained. Alternatively, Perkins Applanation Tonometer (PAT) is also used to measure the intra-ocular pressure. Herein, the PAT is a hand-held tonometer which is ergonomic and easy to use. However, the PAT requires a high level of skill to operate, decrease in stability as the PAT is a hand-held tonometer, and the need for topical application of fluorescein and anaesthetic which may lead to scarring of the surface of the eye.

Furthermore, Tonopen is a form of rebound tonometry to measure the intra-ocular pressure. However, the Tonopen requires numbing drops to anaesthetize the eyes. The Tonopen further comprises a probe that bounces off of the surface of the eye in order to measure the intra-ocular pressure of the eye. Herein, the probe used is conical in structure. Furthermore, the conical structure may accidentally lead to a small scarring on the surface of the eye.

Therefore, in light of the foregoing discussion, there exists a need to overcome the aforementioned drawbacks associated with conventional methods related to measurement of physiological parameters.

SUMMARY

The present disclosure seeks to provide an apparatus for determining physiological parameter. The present disclosure also seeks to provide a method for determining a physiological parameter. An aim of the present disclosure is to provide a solution that overcomes at least partially the problems encountered in prior art.

In one aspect, the present disclosure provides an apparatus for determining physiological parameter, the apparatus comprising:

- an elongated magnetic probe, having a first end, a second end opposite to the first end and a middle section between the first end and the second end;
- a driver coil arranged partially to surround the elongated magnetic probe;
- a measurement coil comprising at least a first section and a second section, and the measurement coil arranged partially to surround the elongated magnetic probe and
- a controller configured to
  - selectively energize the driver coil to create a magnetic force to initiate movement of the elongated magnetic probe to a direction of the first end;
  - measure first induced voltage values over the first section and common induced voltage values over at least one of: the first section and the second section, or over the second section, as a function of time during a time of the movement of the elongated magnetic probe;
  - determine locator values as a function of time by dividing the first induced voltage values with the common induced voltage values;
  - map the locator values as a function of time from the time domain to a spatial domain and
  - calculate from the spatial domain locator values, a first velocity profile of the elongated magnetic probe, and use the calculated first velocity profile of the elongated magnetic probe to determine the physiological parameter.

In another aspect, the present disclosure provides a method for determining a physiological parameter, the method comprising

- energizing a driver coil to move elongated magnetic probe to a direction of a first end of the elongated magnetic probe;
- measuring as a function of time, over a first section of a measurement coil, an induced first voltage;
- measuring as a function of time, over at least one of: a first section and a second section or over the second section of the measurement coil, an induced common voltage;
- determining a first locator value as a function of time by dividing the measured induced voltage values with measured induced common voltage values;
- mapping the first locator values from time domain to a spatial domain;
- calculating from the spatial domain first locator values a first velocity profile of the elongated magnetic probe and
- using the first velocity profile to determine the physiological parameter.

Embodiments of the present disclosure substantially eliminate or at least partially address the aforementioned problems in the prior art, and enable to accurately determine the position of the elongated magnetic probe by calculating the induced voltages Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
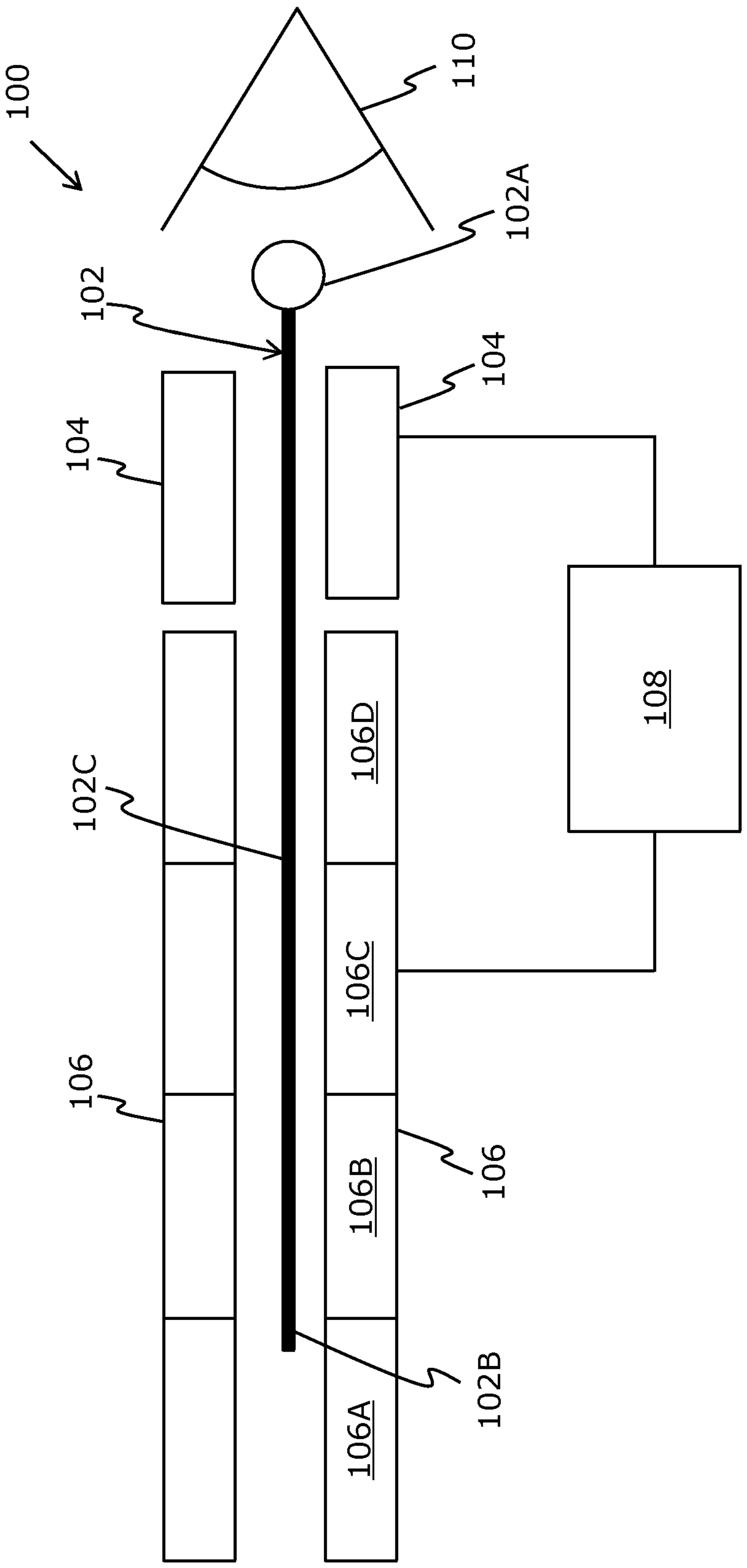
FIG. 1 is a block diagram of a system for an apparatus for determining physiological parameter, in accordance with an implementation of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a An apparatus for determining physiological parameter, the apparatus comprising;

- an elongated magnetic probe, having a first end, a second end opposite to the first end and a middle section between the first end and the second end;
- a driver coil arranged partially to surround the elongated magnetic probe;
- a measurement coil comprising at least a first section and a second section, and the measurement coil arranged partially to surround the elongated magnetic probe and
- a controller configured to
  - selectively energize the driver coil to create a magnetic force to initiate movement of the elongated magnetic probe to a direction of the first end;
  - measure first induced voltage values over the first section and common induced voltage values over at least one of: the first section and the second section, or over the second section, as a function of time during a time of the movement of the elongated magnetic probe;
  - determine locator values as a function of time by dividing the first induced voltage values with the common induced voltage values;
  - map the locator values as a function of time from the time domain to a spatial domain and
  - calculate from the spatial domain locator values, a first velocity profile of the elongated magnetic probe, and use the calculated first velocity profile of the elongated magnetic probe to determine the physiological parameter.

Preferably the measurement of the voltage values from the first section is done simultaneously during measurement of the common induced voltage. Common induced voltage can be measured over a first section and a second section (i.e. voltage of a first section added to voltage of the second section) or as voltage over the second section. The second section can overlap the first section. In deed one can use several sections of measurement coil and combine their signal voltages in different ways before calculating locator signals that are independent of probe velocity. In an optional embodiment the measurement of first section is done first and the on the other measurement cycle the measurement of the common induced voltage is done. A common start of relative time base (t0) is defined as start of the measurement for both separately.

In another aspect, an embodiment of the present disclosure provides a method for determining a physiological parameter, the method comprising

- energizing a driver coil to move elongated magnetic probe to a direction of a first end of the elongated magnetic probe;
- measuring as a function of time, over a first section of a measurement coil, an induced first voltage;
- measuring as a function of time, over at least one of: a first section and a second section or over the second section of the measurement coil, an induced common voltage;
- determining a first locator value as a function of time by dividing the measured induced first voltage values with respective measured induced common voltage values;
- mapping the first locator values from time domain to a spatial domain;

calculating from the spatial domain first locator values a first velocity profile of the elongated magnetic probe and using the first velocity profile to determine the physiological parameter.

Moreover, velocity and magnetization of the elongated magnetic probe is determined, thereby making the measurements more accurate.

The present disclosure provides an apparatus for determining physiological parameter. Herein the apparatus may refer to an instrument that may be used to measure a physiological parameter of the eye such as, intra-ocular pressure of the eye, touch sensitivity and the like. In an embodiment, the apparatus is a tonometer. Herein, the tonometer is used for measuring intra-ocular pressure from an ophthalmic measurement. Furthermore, the intra-ocular pressure is calculated from a voltage signal representing velocity as a function of time of an elongated magnetic probe rebounded from the surface of an eye. The magnitude of the signal depends on the magnetic strength and speed of the elongated magnetic probe.

The apparatus comprises an elongated magnetic probe, having a first end, a second end opposite to the first end and a middle section between the first end and the second end. Herein, the first end of the elongated magnetic probe is made from bio-compatible material and will collide with surface of the eye when in use. Beneficially, the first part being made of bio-compatible material enables the probe to function in intimate contact with living tissues of the eye causing minimal discomfort or pain. Notably, the bio-compatible material is free from carcinogenicity, toxicity, and is resistive to corrosion. Furthermore, the elongated magnetic probe may be made of thin wire of magnetic material. Herein, the elongated magnetic probe may be for instance 20 millimeters in length and 0.5 millimeter in width. Additionally, the magnetic material in the elongated magnetic probe may be ferromagnetic. Moreover, the movement of the elongated magnetic probe inside a measurement coil produces an induced voltage when it moves. However, the magnetic forces of the elongated magnetic probe are insignificantly small, wherein the elongated magnetic probe is pushed back only by the surface of the eye, with no other force being present.

The apparatus comprises a driver coil arranged partially to surround the elongated magnetic probe. Herein, the driver coil is arranged as a loop through which the elongated magnetic probe can move. Furthermore, the driver coil has finite number of loops. Additionally, the driver coil may be arranged along any point between the first end and the second end. For instance, the driver coil may be arranged closer to the first end. Subsequently, the driver coil moves the elongated magnetic probe when electric current is fed through the driver coil. Furthermore, the driver coil pulls the elongated magnetic probe and projected towards the surface of the eye with a velocity which is equal to product of the electric current fed through the driver coil times the elongated magnetic probe magnetization.

The apparatus comprises a measurement coil comprising at least a first section and a second section, and the measurement coil arranged partially to surround the magnetic probe. Herein, the measurement coil has a finite number of loops. Furthermore, the total number of loops of the measurement coil are divided between the first section and the second section. Herein, each of the first section and the second section may have at least one loop through which the elongated magnetic probe is able to move. Furthermore, the elongated magnetic probe may move along the middle section, wherein the middle section is between the first section and the second section. Since the measurement coil comprises two or more sections it is possible to measure at the same time different voltage profiles induced by moving elongated magnetic probe. Technical effect of this is to eliminate uncertainty of magnetization constant of the probe. Indeed, as will be discussed later, making the measurements with at least two different measurement coils allows determination of the velocity of the probe even if the magnetization value is not known at all.

Optionally, the measurement coil is used during first period of time as the driver coil and during a second period of time, which the second period of time is after the first period of time, as the second section of the measurement coil. Herein, the measurement coil is used to drive the electric current, thereby inducing a motion to the elongated magnetic probe. Subsequently, immediately after the elongated magnetic probe is accelerated to its operational velocity, the measurement coil is used to measure induced voltage to the measurement coil. Beneficially, the number of coils in the apparatus is reduced. Furthermore, the measurement coil may have multiple functions depending on the manner a controller controls the measurement coil, such as for example whether electric current is driven or induced voltage is measured.

Optionally, the first section and the second section of the measurement coil are connected in series. Herein, series connection refers to an electrical coupling of the last loop of the first section to the first loop of the second section. Typically, measuring of voltages induced to the measurement coils in a series connection can be realized by connecting a voltmeter to the first section of the measurement coil and the second section of the measurement coil. Alternatively, the induced voltage over the first section is measured. Subsequently, the induced voltage over both the first section and the second section may be measured together to derive total induced voltage value. The voltage value over the second section can be calculated by subtracting from the total induced voltage value of the induced voltage to the first section.

Optionally, the measurement coil comprises a third section, the third section connected in series with the first and the second section of the measurement coil and the third section is arranged to surround a third section of the elongated magnetic probe. Herein, the third section may have at least one loop through which the elongated magnetic probe is able to move. Furthermore, multiple sections may be added in the measurement coil, thereby generating more data points.

In an example, the measurement coil is divided into the first section, the second section, the third section and the fourth section, and the driver coil comprises one section. Herein, a plurality of coupling leads are wired to the points connecting the first section, the second section, the third section and the fourth section of the measurement coil to each other. Furthermore, a first coupling lead is connected to the leftmost end of the first section, a second coupling lead is connected to the junction of the first section and the second section, a third coupling lead is connected to the junction of the second section and the third section, a fourth coupling lead is connected to the junction of the third section and the fourth section, and a fifth coupling lead is connected to the rightmost end of the fourth section. Such exemplary implementation of the measurement coil is further explained in detail in FIG. 6.

The apparatus comprises a controller. Herein, the controller is a computational device that is operable to to respond to and process information. In an example, the controller may be an embedded microcontroller, a microprocessor, computer or a portable computing device. Furthermore, the controller is communicably coupled with the measurement coil and the driver coil. Additionally, the controller energizes the driver coil to move the elongated magnetic probe towards the surface of the eye.

The controller is configured to selectively energize the driver coil to create a magnetic force to initiate movement of the elongated magnetic probe to a direction of the first end. Herein, selectively energizing refers to switching the supply voltage of the driver coil ON or OFF. Notably, an electric field is created when the supply voltage of the driver coil is switched ON. Typically, higher supply voltage of the driver coil will result in greater magnetic force. Subsequently, the acceleration of the elongated magnetic probe will increase. Moreover, the magnetic force is a function of magnetization of the elongated magnetic probe. Herein, the magnetization refers to a strength of magnetisation of the elongated magnetic probe. In particular, higher magnetization will result in greater magnetic force. Additionally, selectively energizing the driver coil will move the elongated magnetic probe towards the surface of the eye. Moreover, the elongated magnetic probe will move in an alternate direction in case polarity of the driver coil by selectively energizing is reversed. Herein, the elongated magnetic probe moves in a direction which may be controlled by the controller whenever required, wherein the voltage is a function of speed of the elongated magnetic probe and magnetization of the elongated magnetic probe. Additionally, the speed of the elongated magnetic probe is monitored continuously by the measurement coil as a function of time. Subsequently, such information relating to the speed of the elongated magnetic probe may be used for determining pressure of the eye which may be used for diagnostic purposes. Typically, a magnetic field is induced in the driver coil when the electric current is provided to the driver coil. Furthermore, the magnetic field is proportional to the electric current and the finite number of loops of the driver coil. Typically, the magnetic field can be controlled by controlling the electric current provided to the driver coil. Subsequently, the magnetic field causes the magnetic force on the elongated magnetic probe, wherein the magnetic force is a function of magnetization of the elongated magnetic probe. Furthermore, acceleration of the elongated magnetic probe can be calculated by dividing mass of the elongated magnetic probe by the force on the elongated magnetic probe. Henceforth, the elongated magnetic probe is accelerated by current pulse in the driver coil, thereby generating a magnetic field acting on the elongated magnetic probe. Furthermore, the elongated magnetic probe is sent through the measurement coil towards the surface of the eye, from which the elongated magnetic probe bounces back. One technical problem of performing above measurements is uncertainty on value of magnetization. Indeed if we compare two probes from different manufacturing patches there can be significant difference between magnetization values or capability to be magnetization of the probes. This would lead to uncertainty when measuring the induced voltages. As an example same induced driver voltage (current) will result to faster movement of the probe as function of magnetization value of the probe.

Optionally, a magnetization cycle can be integrated in the present disclosure for magnetization of the elongated magnetic probe. Herein, the magnetization cycle is achieved by current pulse in the driver coil and the measurement coil respectively, thereby pulling the elongated magnetic probe back and forth in the apparatus. Furthermore, the magnetization cycle may end with a calibration cycle. Herein, the calibration cycle collects the information required to set the acceleration in the driver coil to a value for obtaining an optimal speed for the elongated magnetic probe. Furthermore, the calibration cycle checks both the apparatus and the elongated magnetic probe, before determining the physiological parameter. In one embodiment the calibration cycle can be used to collect lookup table values for mapping collator values as a function of time from the time domain to a spatial domain.

In an embodiment, when in use, the first section of the measurement coil surrounds a first section of the elongated magnetic probe and the second section of the measurement coil surrounds a second section of the elongated magnetic probe, wherein the first section of the elongated magnetic probe is different from the second section of the elongated magnetic probe, when the elongated magnetic probe is in its first spatial position. Herein, the geometrical setup of the apparatus wherein first spatial position is initial position before the elongated magnetic probe is selectively energized. Furthermore, in the first position the elongated magnetic probe is retracted fully inside the apparatus.

Optionally, when in use, the first section of the measurement coil does not surround the first section of the elongated magnetic probe and the second section of the measurement coil surrounds the second section of the elongated magnetic probe, when the elongated magnetic probe is in its second spatial position, which the second spatial position is different from the first spatial position. Herein, the second spatial position may be for example when the elongated magnetic probe is moved to an extreme position, for instance, almost out of the measurement coil. Furthermore, as the first section of the measurement coil does not surround the elongated magnetic probe at all, the change in magnetic flux on the measurement coil is greater as compared to the measurement coil surrounding the elongated magnetic probe partially. Moreover, the magnetic flux is constant for an evenly magnetized elongated magnetic probe throughout. Herein, magnetic flux lines leave from one end, and re-enter from the opposite end. Furthermore, some of the magnetic flux lines pass through the wall of the measurement coil while re-entering from the opposite end. Moreover, the elongated magnetic probe is long and fits closely to the measurement coil so that the magnetic flux in each turn of the measurement coil changes with time.

The electric current in the measurement coil acts on the elongated magnetic probe with a controlled magnetic field pulse, thereby sending the elongated magnetic probe with the desired speed to the surface of the eye. Herein, the speed of the elongated magnetic probe is determined by the amplitude of the current pulse, length and the magnetization of the elongated magnetic probe, and friction between the elongated magnetic probe with the measurement coil and the driver coil respectively. Furthermore, the elongated magnetic probe bounces back when it hits the surface of the eye. Moreover, the intra-ocular pressure can be determined by measuring the speed profile of the elongated magnetic probe, while the elongated magnetic probe is approaching, rebounding, and or returning.

The controller is configured to measure first induced voltage values from the first section and common induced voltage values, as a function of time during a time of the movement of the elongated magnetic probe. Herein, when the elongated magnetic probe moves inside the loops of the first section and the second section, voltage is induced as per Faraday's law of induction. Furthermore, the controller is configured to measure the first induced voltage value as function of time during the movement of the elongated magnetic probe over the first section. Additionally, the common induced voltage of the measurement coil as a function of time is measured. The common induced voltage in case of having two sections (the first section and the second section) is induced voltage over both sections. If there are for example three or four sections the common induced voltage is induced voltage over first, second, third and four sections.

Additionally, optionally, the sampling interval of the induced voltage and the geometry of the measurement coil are controlled by controlling the position of the elongated magnetic probe precisely using the robotic system. Moreover, as the elongated magnetic probe passes through the first section, the second section, the third section and the fourth section towards the surface of the eye, the induced voltage changes as the function of time. Furthermore, the amplitudes of the induced voltage are proportional to the position and velocity of the elongated magnetic probe. Additionally, the common induced voltage is suited for measuring the speed, when the magnetization of the elongated magnetic probe is known. This has been explained further in detail in conjunction with FIG. 4. As discussed one technical problem is that the magnetization of the elongated magnetic problem can have a range of values thus making straightforward calculation of the speed difficult.

Initially, the common induced voltage (and the first induced voltage) increases during the acceleration provided by the driver coil to the elongated magnetic probe. Subsequently, the elongated magnetic probe hits the surface of the eye and decelerates for about 1 millisecond (ms) to zero after from 20 milliseconds up to 35 millisecond and then bounces back, depending on the exact velocity and distance from the surface of the eye. The deceleration of the elongated magnetic probe may for example be carried out at 20, 24, 28 or 32 milliseconds up to 21, 25, 30 or 35 milliseconds. Herein, the trajectory of the speed of the elongated magnetic probe during contact with the surface of the eye is mainly dependent on the speed of the elongated magnetic probe and, via a pushback force, or intra-ocular pressure. Furthermore, the main parameter for dependence on the intra-ocular pressure is given by the slope of deceleration of the speed of the elongated magnetic probe, wherein deceleration of the speed of the elongated magnetic probe is equal to the magnetic force between the elongated magnetic probe and the surface of the eye. Additionally, the apparatus of the present disclosure provides with some corrections, an output signal from the elongated magnetic probe from which the intra-ocular pressure is derived. Notably, the output signal is verified with patient data, using other types of measurements, to generate a curve to translate to reveal the true intra-ocular pressure. Consequently, with the exception at low intra-ocular pressures, the intra-ocular pressure is equal to approximately a factor of 1.5 times the input signal minus a constant. Moreover, the factor becomes larger and the constant becomes smaller at low intra-ocular pressures. This has been explained further in detail in conjunction with FIG. 3. Furthermore, the first signal amplifier and the second signal amplifier used are operational amplifiers. Herein, the operational amplifiers add voltages at the input of amplifying stage via the resistors to the negative and positive terminals of the first signal amplifier and the second signal amplifier. Furthermore, several induced voltage signals may be easily added or subtracted into a common output with weights set by the resistors. Specifically, a differential amplifier may be used for simple implementation of the present disclosure. Herein, the first input of the differential amplifier is connected to the negative terminal and the second input of the differential amplifier is connected to the positive terminal. Additionally, a basic implementation may be performed using a first amplifier and a second amplifier. Herein, the first amplifier has multiple inputs for addition of selected induced voltage from the first section or the second section or optionally, the third section or the fourth section. Furthermore, the second amplifier is a differential amplifier for calculating the common induced voltage. In an example, the first amplifier is electrically coupled with the second section and the third section, thereby determining the difference between the induced voltages of the second section and the third section. Furthermore, the second amplifier is electrically coupled with the first section and the fourth section, thereby generating the common induced voltage. In an example, the first induced voltage of the first section is referred to as 'V1', the second induced voltage of the second section is referred to as 'V2', and the third induced voltage of the third section is referred to as 'V3'. Furthermore, four resistors 'R1', 'R2', 'R3' and 'R4' are connected to the differential amplifier. In such example, the output voltage $V_{out}$ is calculated as, $$V_{out} = \left(V1 \cdot \frac{R1}{R1+R2} + V2 \cdot \frac{R1}{R1+R2}\right)\left(1+\frac{R4}{R3}\right) - V3 \cdot \frac{R4}{R3}$$

It turns out that for detecting very small signals the method of using differerential amplifiers giving Vout proportional to V1-V3 is practical for removing interfering signals: Such amplifiers are commercially available for this purpose.

Figure 8:
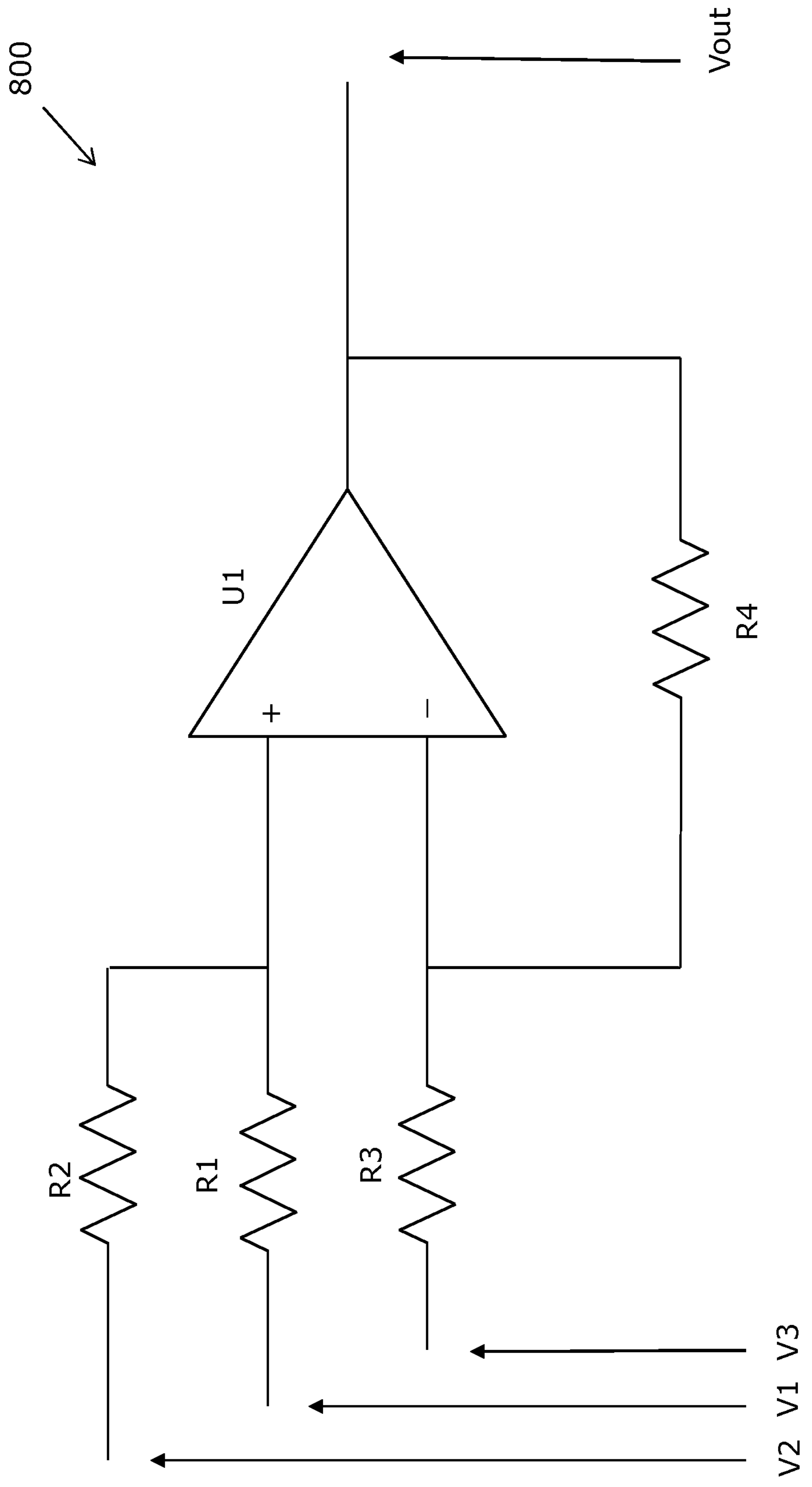
FIG. 8 is an electric circuit to add the induced voltages, in accordance with an implementation of the present disclosure.

Such example is explained further in detail in conjunction with FIG. 8. Furthermore, any combination of induced voltages of the measurement coil can be obtained using an operational amplifier with four inputs or less, by adjusting the sign and amplification factors with the values of the summing resistors. Additionally, using a combination of the outputs of the first amplifier and the second amplifier, an optimized signal may be obtained. Herein, the optimized signal may be sensitised as per requirement, such as for example the position of the elongated magnetic probe, and unsensitized to another parameter, such as for example the degree of magnetization.

The controller is configured to determine locator values as a function of time by dividing the first induced voltage values with the common induced voltage values. Technical effect for dividing (pair wise) first voltage values with respective common induced voltage values is the eliminate unknown magnetization constant of the elongated magnetic probe. In deed introduced voltage is a function of change in magnetic flux @ in a measurement coil. The magnetic flux is a function of magnetic field B i.e. magnetization of the elongated magnetic probe. Since B is constant it can be eliminated by dividing the first induced voltage with the common induced voltage values. The locator values refer to values which are correlated with the actual location of the elongated magnetic probe. Furthermore, the locator values are initially a function of time considering that the measurements are made as a function of time. Thereby, the locator values are in time domain. Furthermore, the first induced voltage value is divided with respective measurement of common induced voltage. Experimentally, division of the first induced voltage coil value with common induced voltage values provides similar formfactor. Consequently, the locator values are independent of the speed of the elongated magnetic probe. Beneficially, the speed of the elongated magnetic probe is the function of magnetization, thereby eliminating variations of electric current of the driver coil on probe magnetization. Typically, the first induced voltage values and the common induced voltage values are measured to solve uncertainty of the magnetization of the elongated magnetic probe. Furthermore, the first induced voltage values and the common induced voltage values are function of velocity and the magnetization of the elongated magnetic probe. In an example, the first signal amplifier measures the common induced voltage of the entire measurement coil for the 0.2 volts (V) driver coil and for a 0.3 V driver coil. Herein, the common induced voltage is referred to as 'U15'. Furthermore, the second signal amplifier is electrically coupled with the second coupling lead of the second section and the fourth coupling lead of the junction of the third section and the fourth section, thereby referred to as 'U24'. However, upon division of 'U24' with 'U15', the result is exactly the same in the case of the 0.2V driver coil as well as the 0.3 V driver coil, by virtue of dependency on the amplitude of the driver coil being factored out. Particularly, the speed of the elongated magnetic probe directly affects the induced voltages. Herein, the second induced voltage values have increased by 1.6, and the locator values in the middle range are the same within the accuracy of the measurement. Furthermore, voltage signals below Z=5 millimetres (mm) and above Z=10 millimetres are not considered, as the induced voltage values have not changed rapidly as a function of Z and the locator values are constant. This has been explained further in detail in conjunction with FIG. 11.

Continuing with the previous example, the useful range is mostly towards the left and becomes narrower. Thereby, the present disclosure may be implemented as per requirements. Herein, the useful range may be widened by using a fourth signal amplifier, a fifth signal amplifier and so forth. This has been explained further in detail in conjunction with FIG. 12. FIG. 13 shows the signals collected for the case of using two amplifiers in a way that covers a wide region centered to the region of interest. The U15 signal is measured by summing the output signals from the first signal amplifier and the second signal amplifier. Herein, the summation of the output signals from the first signal amplifier and the second signal amplifier is referred to as 'U+'. Furthermore, the difference between the output signal from the first signal amplifier and the second signal amplifier is referred to as 'U−'. Typically, the locator values are calculated by the ratio of the difference of the output signals from the first signal amplifier and the second signal amplifier by the sum between the output signals from the first signal amplifier and the second signal amplifier, $$L = \frac{U-}{U+}$$

The controller is configured to map the voltage U13 and U35 as a function of time. Herein, the time domain refers to the locator values as a function of sampling time. Furthermore, mapping may be executed by using, such as for example a lookup table, wherein the locator values are determined by experiments for each geometry of the measurement coil. Herein, this can be implemented, such as for example by moving the elongated magnetic probe back and forth with the actuator, and simultaneously measuring the induced voltage values. In view of the fact that the movement is done with the driver coil, relationship between the induced voltage values and spatial positions of the elongate magnetic probe can be determined.

Optionally, the time domain to spatial domain is mapped by at least one of: pre-determined transfer function or a look up table. The mapping of time domain signals is, for instance, done by placing the probe in exact locations and vibrating it with a very small displacement at a suitable frequency, of the order of 1 kilohertz. The time domain signal at this location is proportional to the induced voltage at 1 KHz. This is done in order to calibrate location curve. Mapping to the spatial domain from the time domain is needed step in order to determine velocity of the probe. Creation of the pre-determined transfer function is disclosed in example 1 below and example of how to determine a look up table is in example 2.

The controller is configured to calculate from the spatial domain locator values, a first velocity profile of the elongated magnetic probe, and use the calculated first velocity profile of the elongated magnetic probe to determine the physiological parameter. Herein, the first velocity profile is calculated from the locator values in the time domain against the locator values in the spatial domain. Moreover, depending on the target application, the velocity as the function of time is used to determine the physiological parameter, such as for example the intra-ocular pressure. In an example, the speed of the elongated magnetic probe and the response of the surface of the eye to stop the elongated magnetic probe once it is ejected towards the surface of the eye may be determined by calculating first derivate of the velocity. Furthermore, the speed of the elongated magnetic probe rebounding from the surface of the eye may be determined. Herein, the intra-ocular pressure is high in case the elongated magnetic probe rebounds rapidly, and the intra-ocular pressure is low in case the elongated magnetic probe rebounds slowly. Subsequently, the measurements regarding the time and velocity of the elongated magnetic probe may be collected with medical trials and function of speed of the elongated magnetic probe formfactors is compared with medical trial measurements as discussed in the present disclosure to determine physiological parameters. Furthermore, the speeds of the elongated magnetic probe may be determined by dividing the first induced voltage value to the second induced voltage value, thereby giving a relative value which is used to determine the speed of the elongated magnetic probe. Optionally, wherein the first velocity profile comprises at least one of: a velocity in the spatial domain, a velocity in the time domain. Optionally, the second velocity profile comprises at least one of: a velocity in the spatial domain, a velocity in the time domain.

It will be appreciated that the present disclosure does not intend to limit the scope of the apparatus to measurement of a physiological parameter of the eye. Notably, the apparatus may be employed to measure a physiological parameter relating to any part of the body in a manner similar to as described with respect to the eye surface.

Optionally the controller of the apparatus is further configured to measure a second induced voltage values from a section other than the first section, as a function of time during a time of the movement of the elongated magnetic probe;

determine a second locator values as function of time by dividing the second induced voltage values with the common induced voltage values;

map the second locator function from a time domain to a spatial domain;

calculate from the spatial domain second locator values a second velocity profile of the elongated magnetic probe and use the calculated second velocity profile the elongated magnetic probe to update the physiological parameter. Updating can be done for example by calculating average between the first velocity profile and the second velocity profile and use the average as the velocity profile to determine physiological parameter.

The present disclosure also relates to the method as described above. Various embodiments and variants disclosed above apply mutatis mutandis to the method.

Optionally, the elongated magnetic probe is directed to move towards a patient to hit a surface of the patient body and bounce back thereof. The surface can refer to surface of eye of the patient. By directing the probe to surface and measuring velocity profile gives indication for example of eye pressure of the patient. If, for example, velocity profile indicates decreased acceleration when the probe hits the eye it is indication of low eye pressure. Higher acceleration (i.e. change of speed profile) can indicate higher eye pressure.

Optionally, the measurements are carried out during the movement of the elongated magnetic probe to obtain induced voltage values as function of time.

Optionally, the determination of the physiological parameter is carried out at least by one of: analysing acceleration of the elongated magnetic probe during its impact to the surface of the patient body, change of velocity before the impact and after the impact, amount of penetration of the elongated magnetic probe to the surface of the body. Acceleration can be determined from the velocity profile as the acceleration is derivate of the velocity in respect to time.

Optionally, the physiological parameter value is updated by measuring as a function of time, with a section of a measurement coil different from the first section, a second induced first voltage;

determining a second locator values as function of time by dividing the second induced voltage values with the common induced voltage values;

mapping the second locator function from a time domain to a spatial domain;

calculating from the spatial domain second locator values, a second velocity profile of the elongated magnetic probe as function of location;

using the calculated second velocity profile for updating the physiological parameter.

Optionally, the first velocity profile comprises at least one of: a velocity in the spatial domain, a velocity in the time domain.

Optionally, the second velocity profile comprises at least one of: the velocity in the spatial domain, the velocity in the time domain.

Example 1: Creating of Pre-Determined Transfer Function by Experiments

Furthermore, mapping of locator values is executed to obtain the localization, that is the value of Z and velocity dZ/dt of the probe. Mathematically, the elongated magnetic probe is mapped into linear space with Z for the position, wherein to measure a first function L with respect to Z, a robotic system is used for setting the value of Z and for mapping. Herein, the first function L with respect to Z is referred to as 'L(Z)'. Additionally, a second function L with respect to Z is determined such that the second function is dependent on position of the elongated magnetic probe, and is independent of the signal coil induced voltage signal, the degree of the elongated magnetic probe magnetization and the probe velocity. Moreover, time derivative of Z is used for calculating the velocity (v) of the elongated magnetic probe, $$v = dZ/dt = (dL/dt)/dL/dZ)$$

For instance, for an elongated magnetic probe moving at fast speeds, the locator values are sampled with a short time interval, where in the short time interval is given by the formula $T_n$–$T_n$–1. Herein, 'n' denotes a finite time interval. Additionally, the locator values will increase correspondingly, which is given by the formula, $L_n$–$L_n$–1. Therefore, the velocity of the elongated magnetic probe for the $n^{th}$ sample is given by $$v_n = \frac{K(L_n - L_n - 1)}{T_n - T_n - 1}$$

Furthermore, data points can be collected while making long sweeps of Z-values, starting at Z=0, and thereby making several steps each of 1 mm. Herein, the voltage signals are root mean square value of the measured voltage in millivolt (mVrms) at the output of the digital oscilloscope. Notably, the range of Z giving useful locator values is 1 to 7, this is limited by the largest distance allowed to the eye being probed, in order to get a dependable result. Furthermore, data from a range of points is used for fitting the localization curve, wherein the data for first ten points are collected for U+ voltage and U− voltage, respectively. Additionally, the first five Z-values are calculated from the given data. This has been explained further in detail in conjunction with FIG. 13C. Subsequently, values as provided in table of FIG. 13D were observed. Furthermore, by removing the speed, the magnetization and the dependence of the elongated magnetic probe on the first induced voltage value, the second induced voltage value, the third induced voltage value and the fourth induced voltage value, and dividing them point by point with the common induced voltage, the position of the elongated magnetic probe is obtained. Additionally, a suitable linear combination may be created with the help of the measurements. This has been explained further in detail in conjunction with FIG. 5

Example 2: An Example of how to Determine Above Mentioned Look-Up Table by Moving the Elongated Magnetic Probe Back and Forth In the present disclosure, the first induced voltage used for indicating the speed of the elongated magnetic probe is induced in the measurement coil by vibrating the elongated magnetic probe using a vibrator. Herein, the vibrator vibrates the elongated magnetic probe at a frequency of 875 hertz (Hz), using a commercial piezoelectric device at its mechanical resonance frequency. Typically, the amplitude of the vibration of the vibrator is small. Notably, the vibrator is driven by setting a signal generator to 0.2 volt (V) and 0.3 V, respectively. Moreover, the common induced voltage is the sum of the induced voltages of the measurement coil. Additionally, the sum of the voltages of the first section and the second section may be measured by measuring the induced voltage of the first section and the second section separately.

Optionally, the common induced voltage is measured over all sections of the measurement coil. Herein, at least the first section and the second section of the measurement coil are connected with a first signal amplifier and a second signal amplifier. Furthermore, the first signal amplifier and the second signal amplifier comprise differential inputs that may be modified as per requirement. In an exemplary implementation, the first signal amplifier is connected between the first section and the third section, and the second signal amplifier is connected between the third section and the fourth section. Furthermore, the vibrator produces signals from the first signal amplifier and the second signal amplifier below 1 volt (V), which is low enough to avoid saturation. Typically, 500 root mean square of the measured voltage in millivolt (mVrms) is the output for the driver coil, wherein standard voltage of the driver coil is 0.2 V. Furthermore, 800 mVrms is the output for the driver coil whose standard voltage is 0.3V. Additionally, the inputs of the first signal amplifier and the second signal amplifier are connected to the plurality of coupling leads of the measurement coil, wherein the measurement coil corresponds to about 1 millivolt (mV) and 1.6 mV respectively. In addition, the outputs of the first signal amplifier and second signal amplifier respectively are connected to inputs of a digital oscilloscope for measuring the speed of the elongated magnetic probe. Particularly, induced voltages are obtained from the four sections of the measurement coil. Herein, induced voltage obtained between the first coupling lead and the second coupling lead is referred to as 'U12', voltage obtained between the second coupling lead and the coupling lead is referred to as 'U23', voltage obtained between the third coupling lead and the coupling lead is referred to as 'U34', and voltage obtained between the fourth coupling lead and the fifth coupling lead is referred to as 'U45'. Herein, the measurements are taken over a train of 30 magnetization cycles, by manually triggering the signal generator using the 0.2 V driver coil or the 0.3 V driver coil at 875 hertz (Hz), wherein the signal generator is connected to the driver coil through a third signal amplifier. Consequently, the digital oscilloscope measures the root mean square value of the output from the first signal amplifier and the second signal amplifier and saves it digitally into a spreadsheet. Herein, the spreadsheet comprises visual basic code for receiving and displaying the measurements as a function of the position of the elongated magnetic probe. Additionally, the position of the elongated magnetic probe is determined by integrating the speed over time. Optionally, the position of the elongated magnetic probe is controlled by a robotic system. Herein, the robotic system comprises a linear screw driven by a step motor, allowing the elongated magnetic probe move linearly with a high accuracy. Beneficially, slow movement of the measurement coil does not induce a voltage in the signal coil. Furthermore, the robotic system steps the position between measurements. Herein, the position of the elongated magnetic probe is referred to as 'Z'. Additionally, the mechanical end position is starting position, Z=0. Furthermore, the robotic system is also triggered to step 1 millimetre (mm) for the next point to be measured. This has been explained further in detail in conjunction with FIG. 7.

In an implementation of the present disclosure, the locator values were observed to be linear in a range of Z=1 to 5 millimetres (mm). (Z being distance of probe moving in respect to coils). Notably, the trend line is fit using the spreadsheet to the points in the range of Z=1 millimetre to 5 millimetres, thereby providing a close approximation. Furthermore, the resulting trend line of the locator values, has the form of general equation of the straight line, y=mx+c. Additionally, the trend line represents the position of the elongated magnetic probe in the range of Z=1 millimetre to 5 millimetres for doing measurement in the apparatus. Herein, variables 'x' and 'y' are chosen for further calculations. Subsequently, variable x is made equivalent to Z and variable y is made equivalent to 1000 times of the function of L(Z), in order to fit with the coordinates in the present disclosure. Therefore, the equation of the trend line is given by $$1000L = -mZ + c$$

Herein, the value of Z is calculated by inversion of the previous equation $$Z = -\left(\frac{1000}{m}\right)L + \frac{c}{m}$$

Herein, $$K = \frac{-1000}{m},$$

wherein K is a constant. Furthermore, c/m is a value of Z for L=0. Subsequently, $c/m=Z_0$. Hence, $$V = K\left(\frac{dL}{dt}\right),$$

wherein V is a variable. Consequently, $$Z = -VT + Z_o$$

Thus based on the example and example test we are able to determine from the locator values velocity profile of the elongated magnetic probe. The velocity profile can be used to determine a physiological parameter. I.e the speed of the elongated magnetic probe may be used to determine the physiological parameters. Notably, the first induced voltage is proportional to the speed of the elongated magnetic probe

DETAILED DESCRIPTION OF THE DRAWINGS

Referring to FIG. 1, there is shown a block diagram of an apparatus 100 for determining physiological parameter, in accordance with an implementation of the present disclosure. The apparatus 100 comprises an elongated magnetic probe 102, a driver coil 104, a measurement coil 106 and a controller 108. The elongated magnetic probe has a first end 102A, a second end 102B opposite to the first end 102A and a middle section 102C between the first end 102A and the second end 102B. Furthermore, the driver coil 104 is arranged partially to surround the elongated magnetic probe 102. Additionally, a measurement coil 106 comprises at least a first section 106A and a second section 106B, and the measurement coil 106 is arranged partially to surround the elongated magnetic probe 102. In the figure the measurement coil comprises 4 sections, the first section 106A, the second section 106B, a third section 106C and a fourth section 106D. Sections are connected with each other's in series. Herein, a controller 108 is communicably coupled with the driver coil 104 and the measurement coil 106. Herein, the controller 108 selectively energizes the driver coil 104 to create a magnetic force to initiate movement of the elongated magnetic probe 102 towards an eye 110. FIG. 1 illustrates probe at position Z=0. As an example a first induced voltage can be measured over the first section 106A. Common induced voltage can be measured over the first section 106A and the second section 106B. Other example is to measure the first induced voltage over the second section 106B and the common induced voltage for example over all four sections. Indeed the term "first section" can refer to any section. The common induced voltage is measured from at least some section(s) which are also different from the first section.

Figure 2:
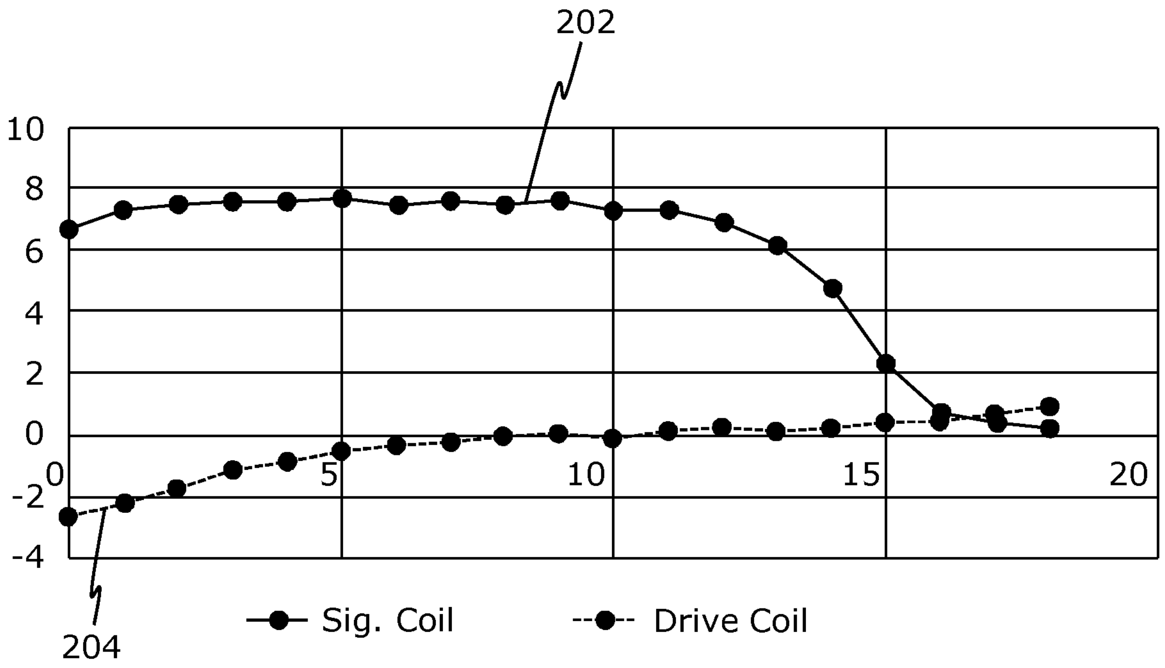
FIG. 2 is a graph to depict a force on elongated magnetic probe induced per ampere of current in signal or drive coil versus position in millimeters.

Referring to FIG. 2, there is shown a graph to depict a force on elongate magnetic probe 102 induced per ampere of current in signal or drive coil versus position in millimeters, in accordance with an implementation of the present disclosure. Herein, horizontal axis represents the magnetic force acting on the elongated magnetic probe 102 induced for 1 ampere (A) of electric current in the measurement coil 106 and the driver coil 104. The vertical axis represents the position of the elongated magnetic probe 102 in millimeters. Furthermore, the line 202 illustrates the magnetic force acting on the elongated magnetic probe 102 by an electric current in the measurement coil 106. Furthermore, the line 204 illustrates the magnetic force acting on the elongated magnetic probe 102 by an electric current in the driver coil 104. The upper curve 202 corresponds to the single signal coil used in present instruments, the lower one 204 to the drive coil. The curves for signal voltages induced by a probe moving at constant velocity in the coils look the same.

Figure 3:
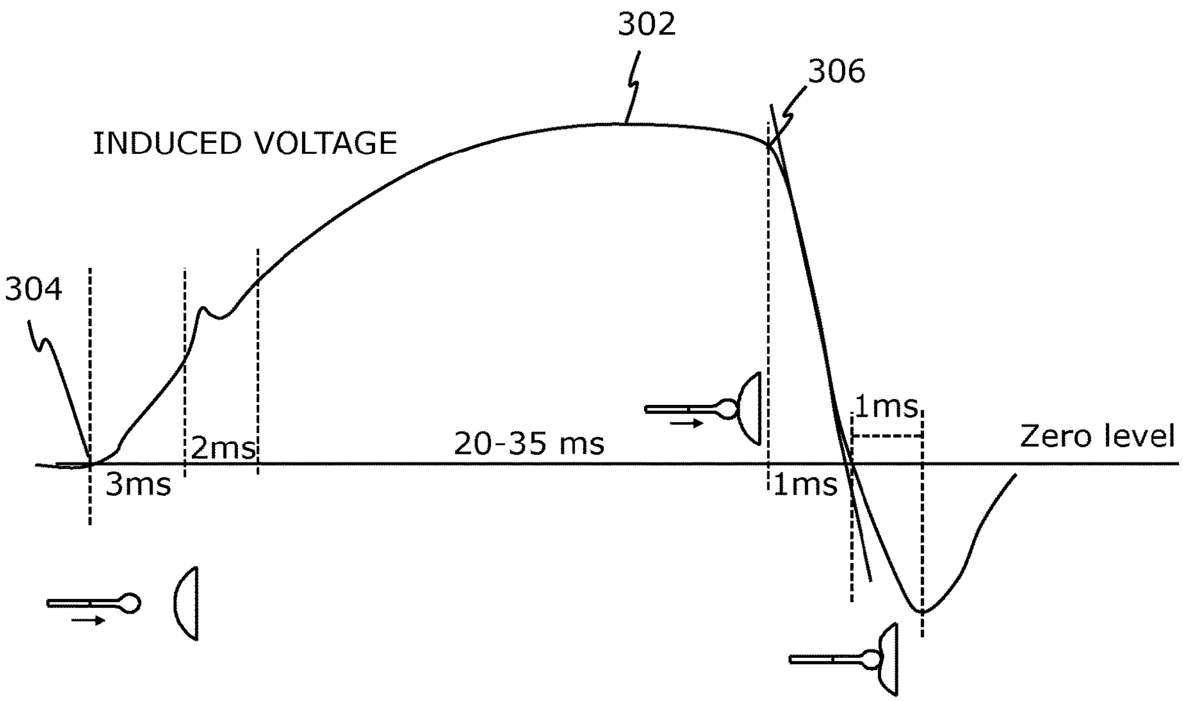
FIG. 3 is a graph to represent the common induced voltage of the measurement coil.

Referring to FIG. 3, there is shown a graph 302 to determine the common induced voltage of the measurement coil 106, in accordance with an implementation of the present disclosure. Herein, the common induced voltage is a function of time. At point 304, the common induced voltage increases as the driver coil 104 begins to accelerate the elongated magnetic probe 102 (starting from position Z=0 mm). Subsequently, the elongated magnetic probe 102 hits the surface of the eye 110 at point 306 (at said when the position is between Z=4 to 8 mm) and decelerates for about 1 millisecond (ms) to zero after from 20 ms up to 35 ms and then bounces back, depending on the exact velocity and distance from the surface of the eye 110. Herein, the trajectory of the speed of the elongated magnetic probe 102 during contact with the surface of the eye 110 is mainly dependent on the speed of the elongated magnetic probe 102 and, via a pushback force, on intra-ocular pressure. Furthermore, the main parameter for dependence on the intra-ocular pressure is given by the slope of deceleration of the speed of the elongated magnetic probe 102, wherein deceleration of the speed of the elongated magnetic probe 102 is equal to the magnetic force between the elongated magnetic probe 102 and the surface of the eye 110. The figure illustrates measurement over a single section of a measurement coil. The drive coil is active at Z<1. The probe hits the eye approximately at Z=5-7 mm were the drive force is close to zero.

Figure 4:
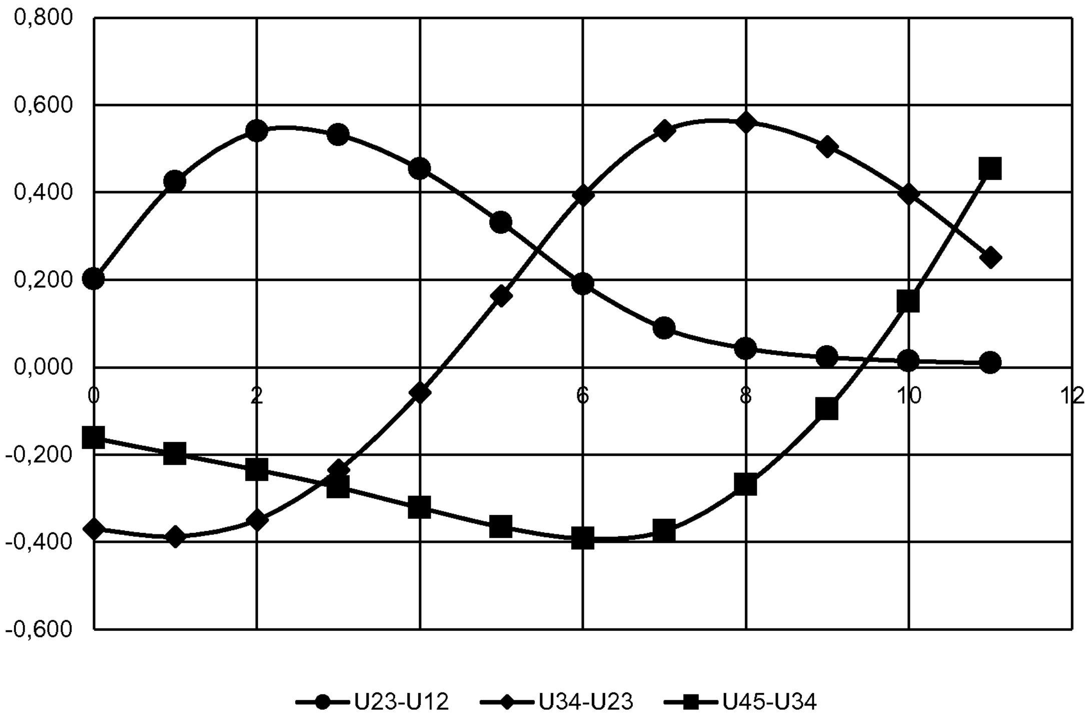
FIG. 4 is a illustration of measurement of three locator signals using four differential amplifiers to measure the voltages across each of the signal coil segments.

FIG. 4 illustrates three locator signals using four differential amplifiers to measure the voltages across each of the signal coil sections. The curves are made by taking signals from adjacent coils, a first section and a second section, the second section and a third section, and the third section and a fourth section, subtracting them pairwise, and dividing them with the sum U+ over all of them (common induced voltage). The curves calculated as described are all independent of probe velocity and magnetization. Selecting between the curves one can localize the probe over a large range. One can also form a suitable linear combination to optimize the sensitivity for a selected region. This setup requires four amplifier/detectors synchronized to sample each point simultaneously by all four channels. Benefit of measuring more than one first induced voltage values is increase of accuracy.

Figure 5:
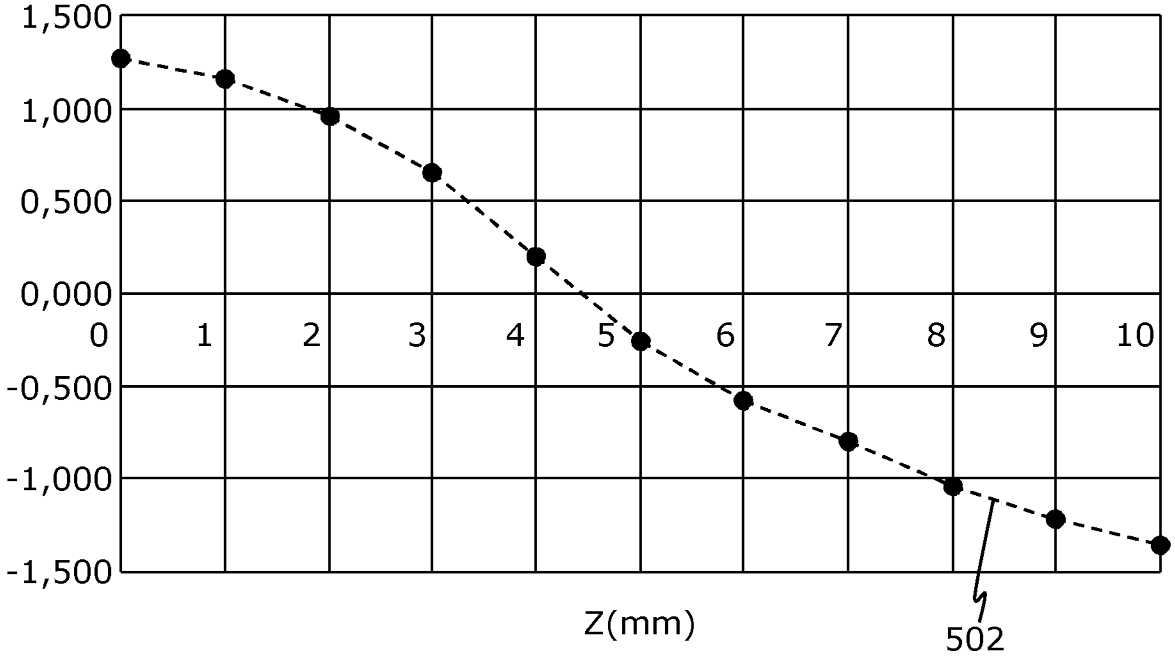
FIG. 5 is a graph to determine the position of the elongated magnetic probe, in accordance with an implementation of the present disclosure.

Referring to FIG. 5, there is shown a graph to determine the position of the elongated magnetic probe 102, in accordance with an implementation of the present disclosure. Herein, the dependence of velocity and magnetization of the elongated magnetic probe 102 are removed by measuring the induced voltage U13 in a half section of the measurement coil (=U12+U23 in FIG. 9) and the one U35 across the other half (=U34+U45). A signal ratio S is calculated as the difference of U13-U34 divided by the common voltage Ucom across the whole coil, which in this case is equal to the sum U13+U34. This signal ratio S represents the position of the elongated magnetic probe 102, and is independent of probe magnetization and velocity. Herein, the horizontal axis represents the position of the elongated magnetic probe 102 in millimeters. Herein, the vertical axis represents the signal ratio S, which is a function of said probe position. Using two signal points, S1 and S2 at times t1 and t2, the curve gives us the corresponding z1 and z2. Using such signal points, the mean velocity of the probe is calculated as $v_{cal}$=(z1−z2)/(t1−t2). Thus we can determine the probe position directly and the probe velocity indirectly, independently of probe magnetization Indeed we can calibrate influence of magnetization and use it to derive probe position and velocity without knowing the magnetization factor of the probe.

Figure 6:
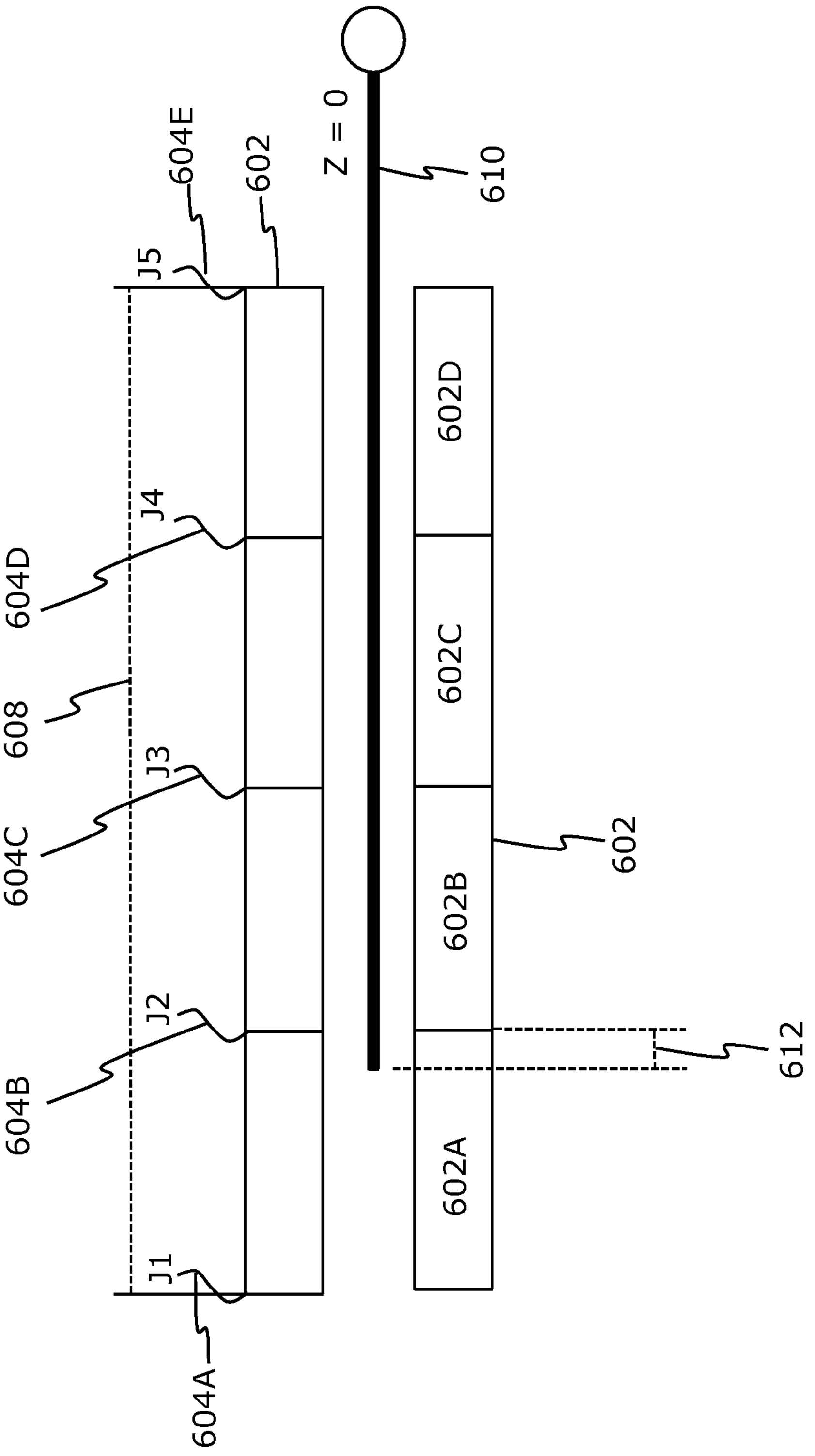
FIG. 6 is an assembly of the measurement coil, in accordance with an implementation of the present disclosure.

Referring to FIG. 6, there is shown an assembly of the measurement coil 602, in accordance with an implementation of the present disclosure. Herein, the measurement coil 602 is split into a first section denoted by 602A, a second section denoted by 602B, a third section denoted by 602C and a fourth section denoted by 602D. Furthermore, a first coupling lead 604A is connected to the leftmost end J1 of the first section 602A, a second coupling lead 604B is connected to the junction J2 of the first section 602A and the second section 602B, a third coupling lead 604C is connected to the junction J3 of the second section 602B and the third section 602C, a fourth coupling lead 604D is connected to the junction J4 of the third section 602C and the fourth section 602D, and a fifth coupling lead 604E is connected to the rightmost end J5 of the fourth section 602D. Additionally, the length of the measurement coil 608 may be 20 millimeters (mm). Moreover, the elongated magnetic probe 610 moves linearly with an accuracy 612 of 1 mm. Herein, Z=0 is the starting position of the elongated magnetic probe 610. In general about notations used in the description following examples are provided: U12 refers to induced voltage between junctions J1 and J2. U16 refers to induced voltage between junctions J1 and J5 (i.e. voltages over all sections 602A, 602B, 602C and 602D). U34 refers induced voltage between junctions J3 and J4. U24 refers to induced voltage between junctions J2 and J4 i.e. over the second section 602B and third section 603C.

Figure 7:
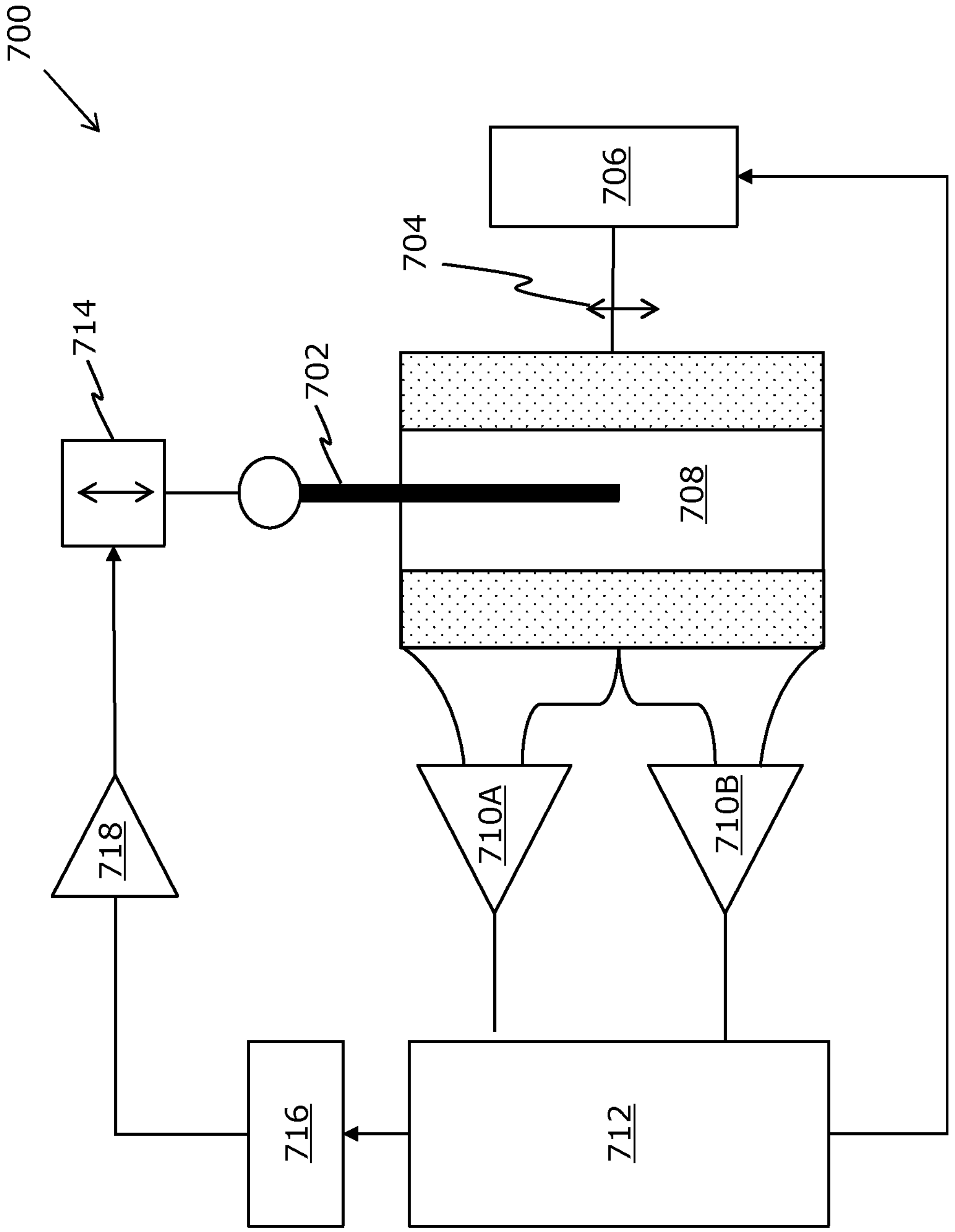
FIG. 7 is a schematic illustration view of a system for a robotic system to determine the speed and position of the elongated magnetic probe, in accordance with an implementation of the present disclosure.

Referring to FIG. 7, there is shown a schematic illustration of a system 700 for a robotic system to determine the speed and position of the elongated magnetic probe 702, in accordance with an embodiment of the present disclosure. Herein, the robotic system comprises a linear screw 704 driven by a step motor 706, allowing the elongated magnetic probe 702 to move linearly inside the measurement coil 708 with better accuracy. Furthermore, a first signal amplifier 710A and a second signal amplifier 710B are used to amplify the induced voltage of the measurement coil 708. Subsequently, the first signal amplifier 710A and the second signal amplifier 710B are electrically coupled with an oscilloscope 712. Additionally, the elongated magnetic probe 702 is vibrated by a vibrator 714 at a frequency of 875 hertz (Hz) to determine the speed of the elongated magnetic probe 702. Herein, the vibrator 714 is driven by a signal generator 716 via a third amplifier 718.

Referring to FIG. 8, there is shown an electric circuit 800 to add the induced voltages, in accordance with an implementation of the present disclosure. Herein, a plurality of resistors are denoted by R1, R2, R3 and R4. Furthermore, a first voltage input connected between the first section and the second section of the measurement coil 708 is denoted by V1, a second voltage input connected at the end of the fourth section of the measurement coil 708 is denoted by V2, a third voltage input connected between the third section and the fourth section of the measurement coil 708 is denoted by V3. Firstly, the first voltage input is negative form of the second induced voltage value, i.e., V1=−U2. Secondly, the second voltage input is the addition of the third induced voltage value and the second induced voltage value, i.e., V2=U3+U4. Thirdly, the third input is equivalent to the third induced voltage, V3=U3. Finally, an output voltage denoted by $V_{out}$ is obtained, wherein the output voltage is the addition of the first input, the second input and the third input $$v_{out} = V1 + V2 + V3 = -U2 + U3 + U4 - U3 = U4 - U2$$

Furthermore, the output voltage may also be calculated with respect to the plurality of resistors, $$V1 = \left(V1 \cdot \frac{R1}{R1 + R2} + V2 \cdot \frac{R1}{R1 + R2}\right)\left(1 + \frac{R4}{R3}\right) - V3 \cdot \frac{R4}{R3}$$

Figure 9:
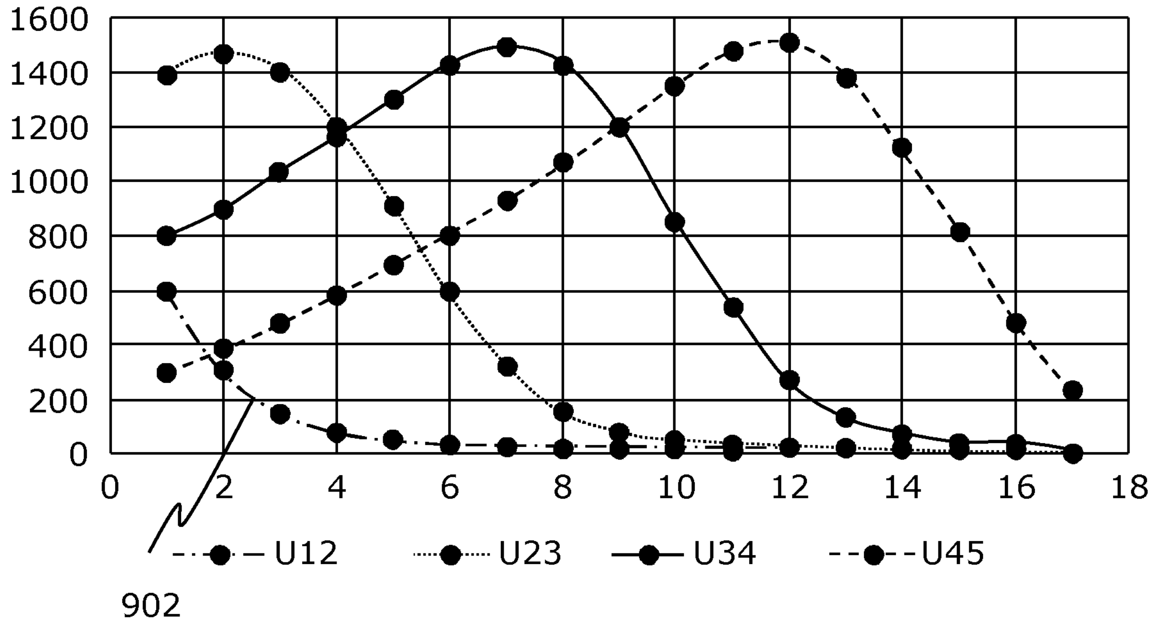
FIG. 9 is induced signal voltages in the measurement coil, in accordance with an implementation of the present disclosure.

Referring to FIG. 9, there is shown induced signal voltages in the measurement coil 602, in accordance with an implementation of the present disclosure. Herein, the vertical axis represents twice the approximated root mean square value in millivolt. Furthermore, the induced voltage obtained between the first coupling lead 604A and the second coupling lead 604B is referred to as U12, voltage obtained between the second coupling lead 604B and the third coupling lead 604C is referred to as U23, voltage obtained between the third coupling lead 604C and the fourth coupling lead 604D is referred to as U34, and voltage obtained between the fourth coupling lead 604D and the fifth coupling lead 604E is referred to as U45.

Figure 10:
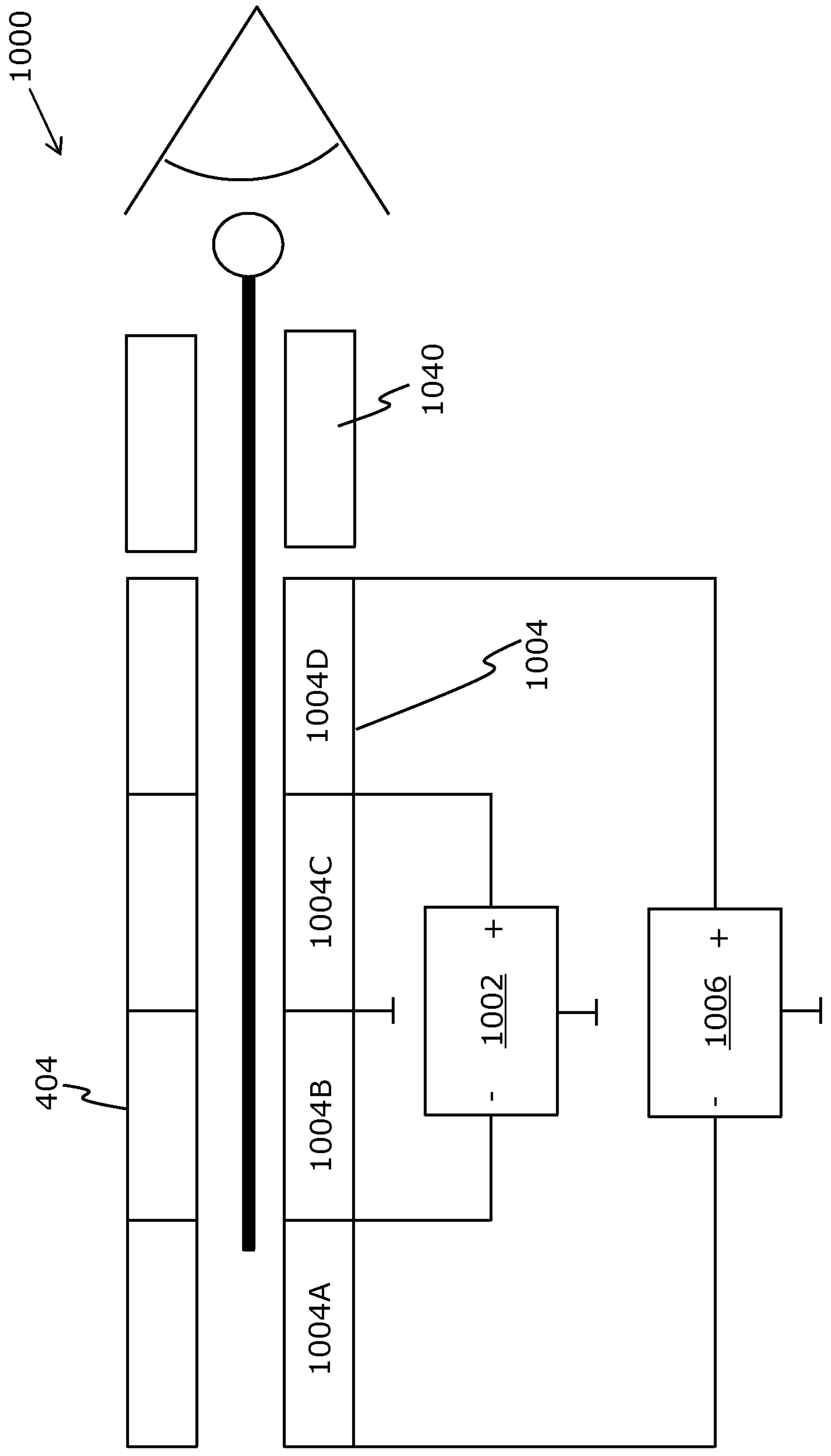
FIG. 10 is a block diagram for a system for basic implementation of the apparatus, in accordance with an implementation of the present disclosure.

Referring to FIG. 10, there is shown a block diagram for a system 1000 for implementation of the apparatus, in accordance with an exemplary implementation of the present disclosure. Herein, a first amplifier 1002 is electrically coupled with the second section 1004B and the third section 1004C of the measurement coil 1004 to measure induced voltages of the second section and the third section to be used as the first induced voltage values. Furthermore, a second amplifier 1006 is electrically coupled with the first section 1004A and the fourth section 1004D of the measurement coil 1004 to determine the common induced voltage. Probe is in position Z=0 in the figure. Probe can be moved with driver coil 1040.

Figure 11A:
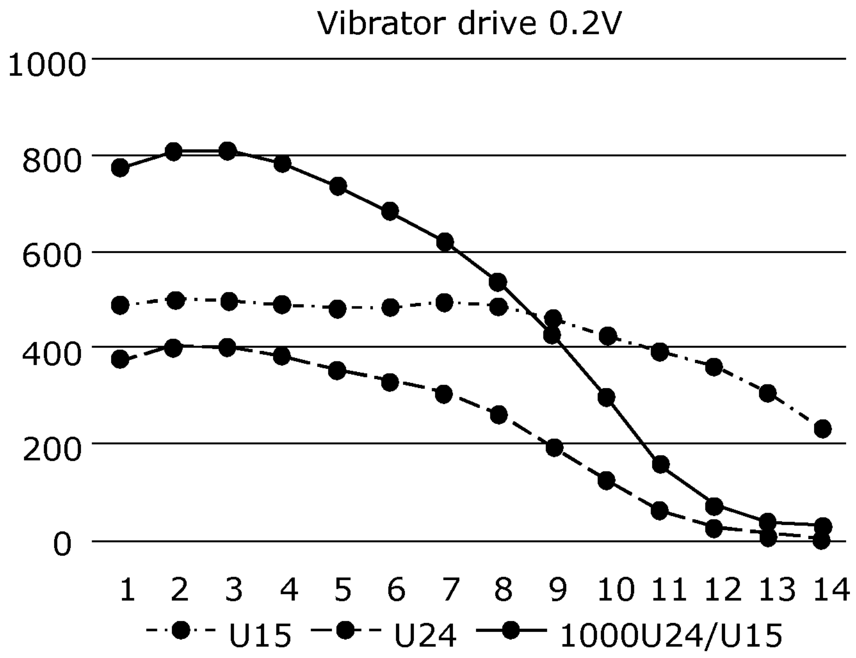
FIGS. 11A and 11B are graphs to realize an optimal connection for the first amplifier and the second amplifier, in accordance with an implementation of the present disclosure.
Figure 11B:
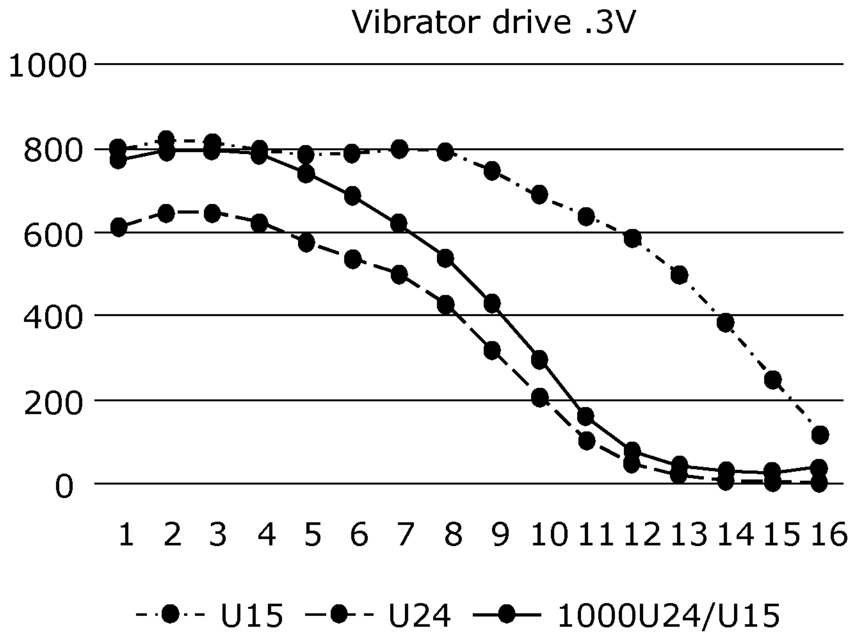

Referring to FIGS. 11A and 11B, there are shown graphs to realize an optimal connection for the first amplifier 1002 of FIG. 10 and the second amplifier 1006 of FIG. 10, in accordance with an implementation of the present disclosure. As shown previously, the first amplifier 1002 is electrically coupled with the second section and the third section of the measurement coil 1004 as shown by the graph of FIG. 10. Furthermore, the second amplifier 1006 is electrically coupled with the first section and the fourth section of the measurement coil 1004. Herein, for a vibrator of 0.2 volts (V), the common induced voltage denoted by U15 is plotted alongside the induced voltage from the second and the fourth section denoted by U24. Furthermore, U24 is divided with U15 to find the optimal connection of the first amplifier 1002 and the second amplifier 1006. Additionally, in FIG. 11B, for a vibrator of 0.3 V, the common induced voltage denoted by U15 is plotted alongside the induced voltage from the second and the fourth section denoted by U24. Furthermore, U24 is divided with U15 to find the optimal connection of the first amplifier 1002 and the second amplifier 1006.

Figure 12A:
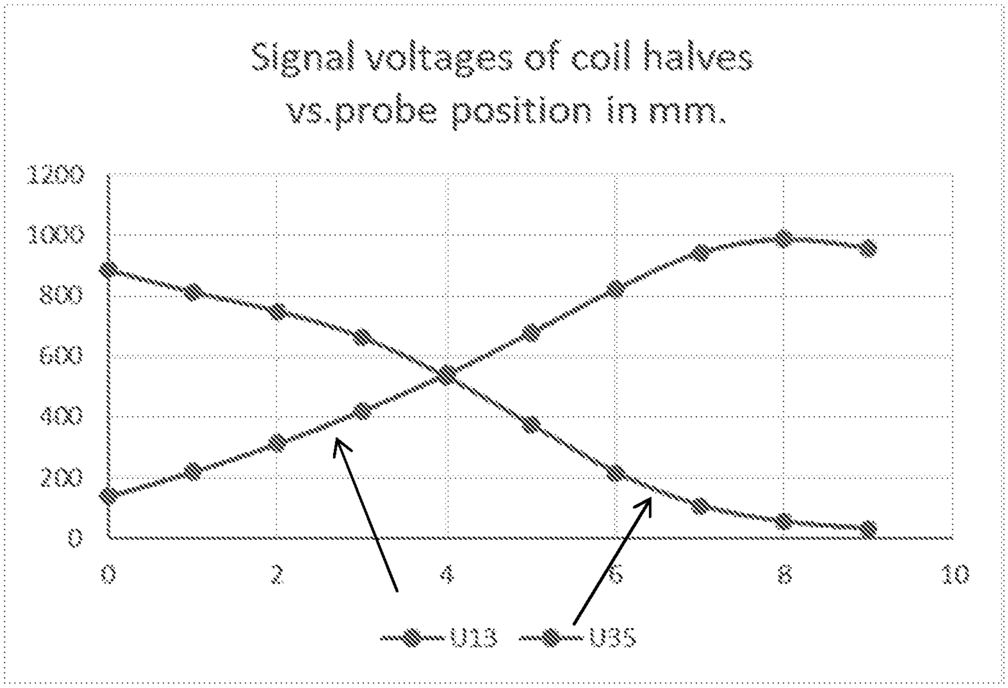
FIGS. 12A and 12B are graphs to illustrate signal voltages and common induced voltage values, in accordance with an implementation of the present disclosure.
Figure 12B:
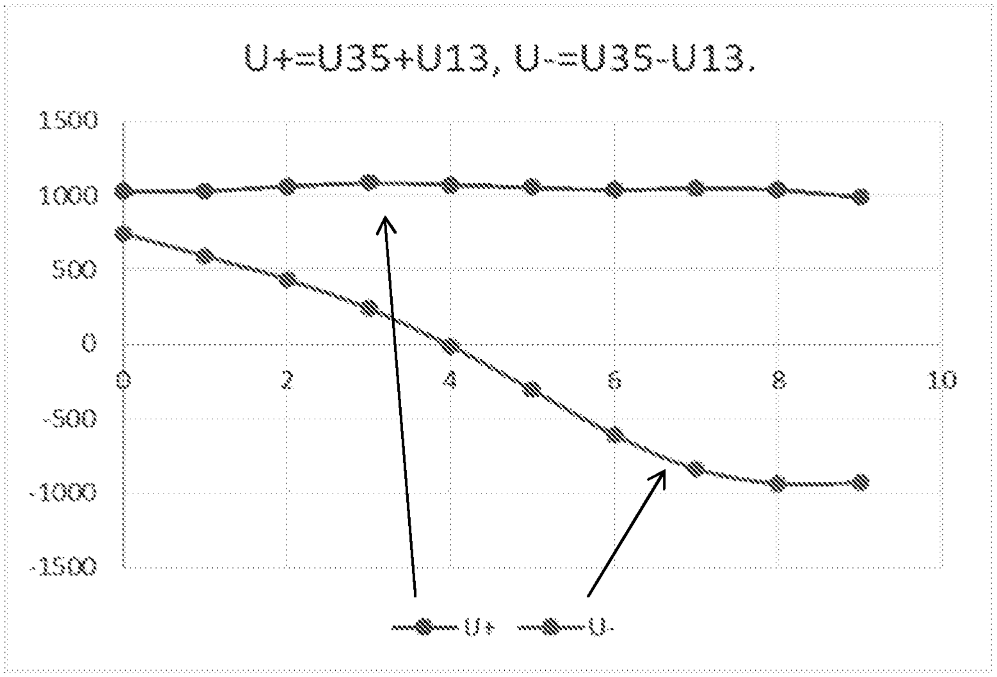

FIG. 12A is an illustration of measured first voltage values U13 and U35. FIG. 12B represents signal voltages, added to represent the total of the signal coil sections (U+), and their difference (U−). Note that U+ is equal to U15: The notation is different just to show that it has been measured by adding two or more measured signals: This is convenient when using them for several purposes, e.g. to form the difference U. A minimal system that would operate like this: The signal coil would have two sections, each with a differential amplifier to generate the signals shown in FIG. 12A. Instead of forming a U− and U+ signal (FIG. 12B), and their quotient (the Locator) one could use the zero-crossing point at 4 mm. Provided that the time for this occurrence has been measured we can calculate the mean speed to go from 0 to 4 mm.

Figures 13A, 13B:
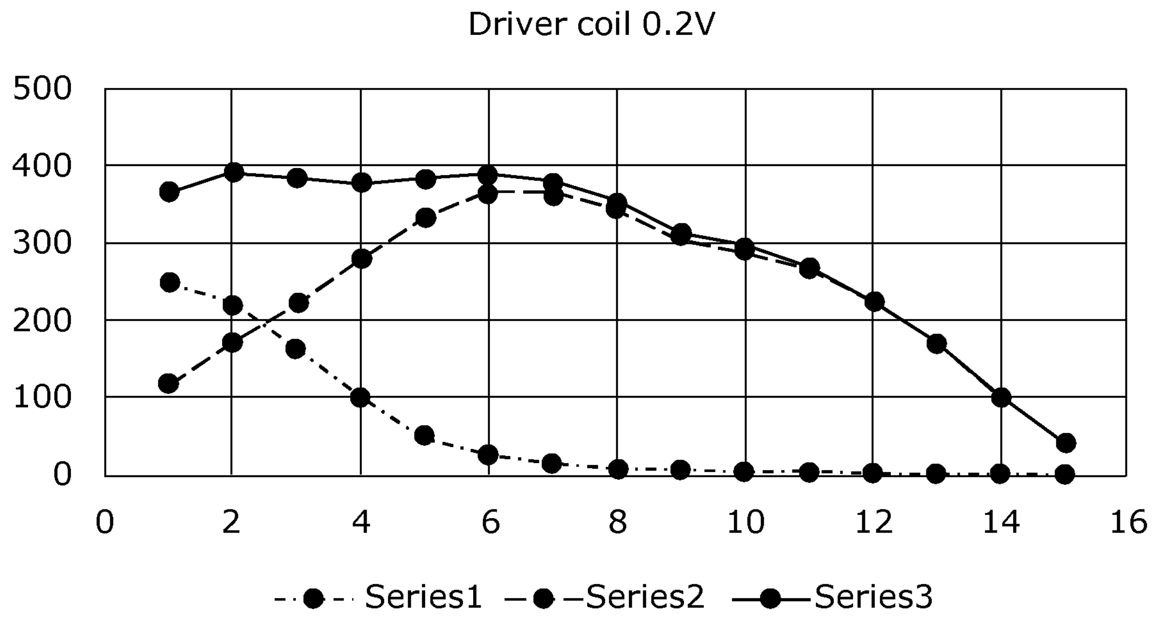
FIGS. 13A to 13D collectively are graphs to measure the locator values by the addition of plurality of signal amplifiers, in accordance with an implementation of the present disclosure.
Figures 13C, 13D:
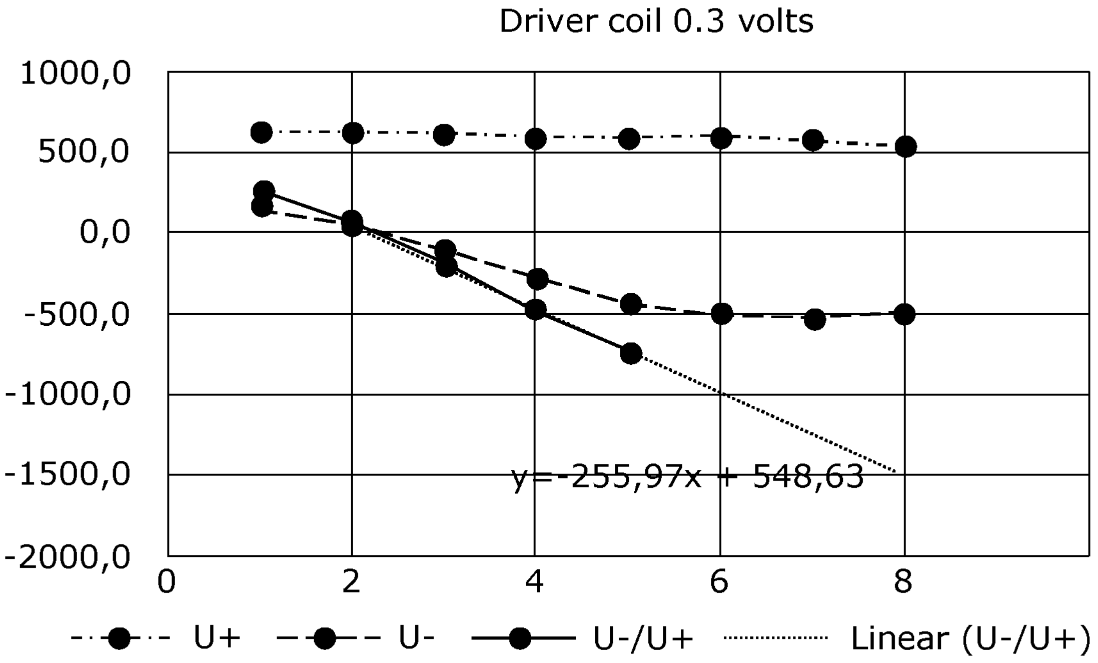

Referring to FIGS. 13A to 13D, there is shown graph to measure the locator values by the addition of plurality of signal amplifiers, in accordance with an implementation of the present disclosure. In FIG. 13A, the line 'Series 1' denotes U13, wherein U13 is the induced voltage in the measurement coil 602 between the first coupling lead 604A and third coupling lead 604C. Similarly, the line 'Series 2' denotes U35, wherein U35 is the induced voltage in the measurement coil 602 between the third coupling lead 604C and the fifth coupling lead 604E. Furthermore, the line 'Series 3' is U+, i.e., summation of the output signals from the first signal amplifier and the second signal amplifier. Furthermore, U− is the difference between the output from the first signal amplifier and the second signal amplifier. FIG. 13B provides locator values with respect to U+ and U−. Notably, the locator signal is generated by dividing U− by U+. Furthermore, FIGS. 13A and 13B provide data while making long sweep of Z-values. Similarly, FIG. 13C provides data from the range of induced voltage values used for fitting trend line. FIG. 13D provides locator values with respect to U+ and U−.

Figure 14A:
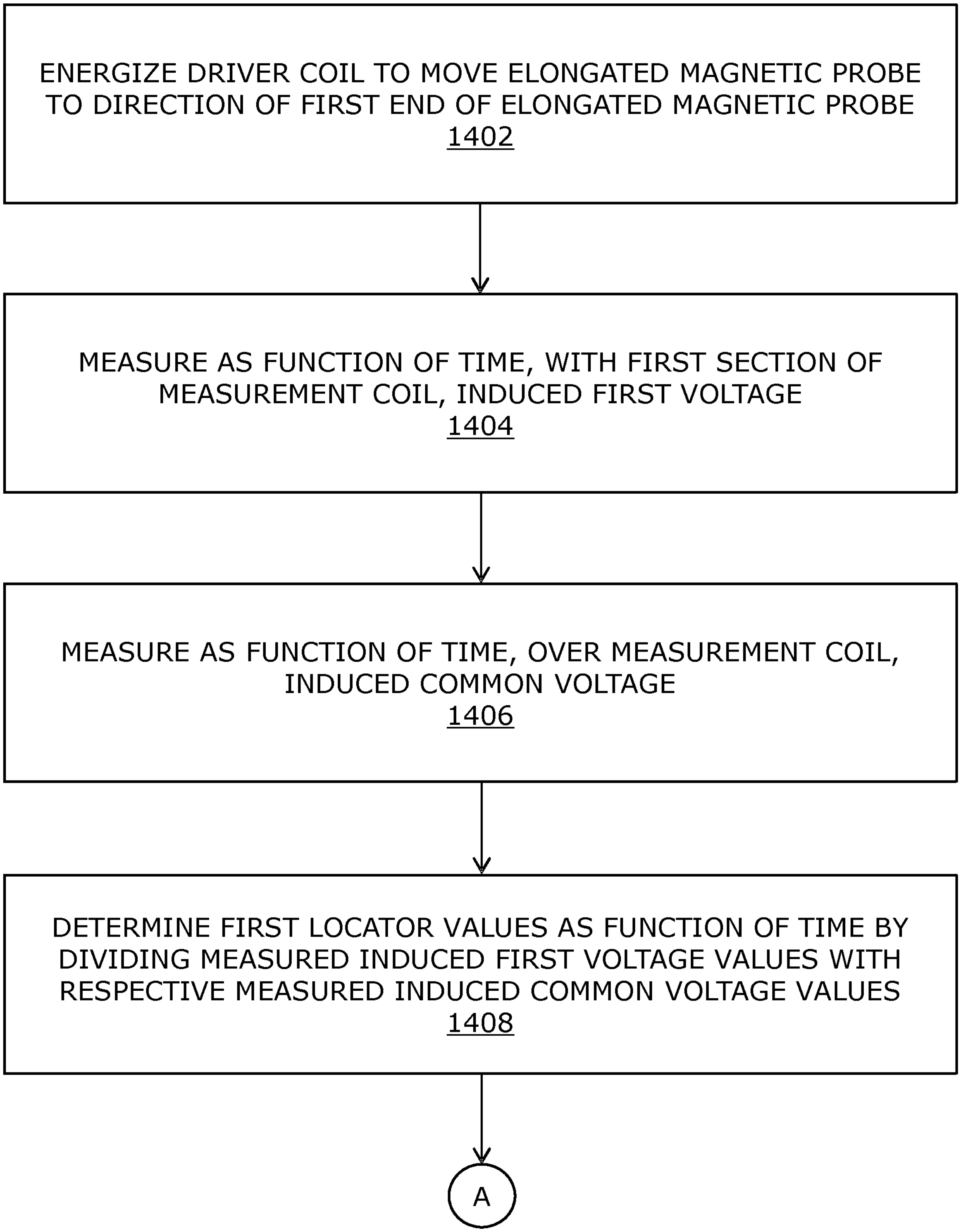
FIGS. 14A and 14B collectively illustrate a flowchart depicting steps of a method for determining a physiological parameter, in accordance with an embodiment of the present disclosure
Figure 14B:
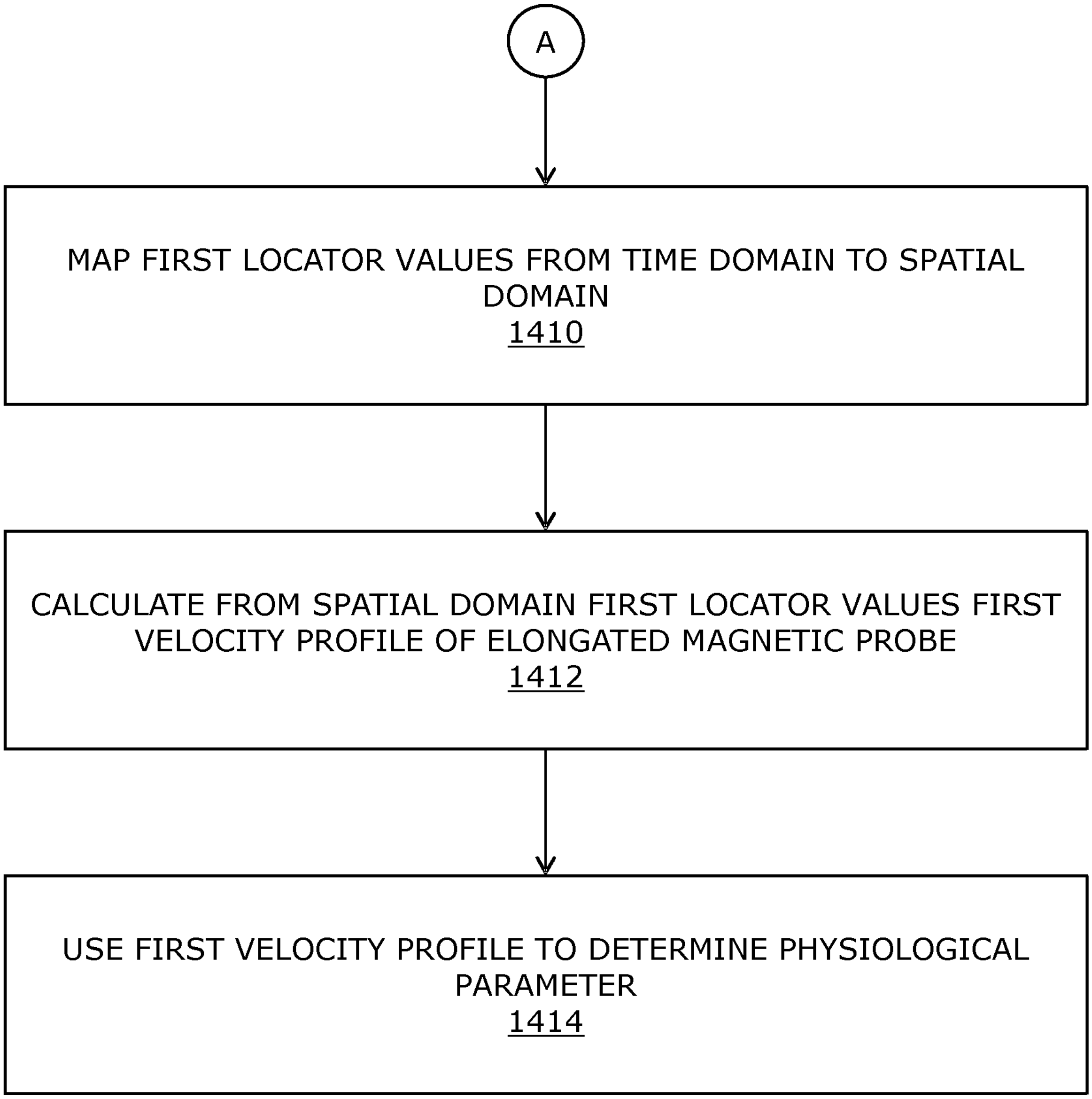

Referring to FIGS. 14A and 14B collectively illustrate a flowchart depicting steps of a method for determining a physiological parameter, in accordance with an embodiment of the present disclosure. At a step 1402, a driver coil is energized to move an elongated magnetic probe to a direction of first end of the elongated magnetic probe. At a step 1404, an induced first voltage is measured as a function of time, with a first section of a measurement coil. At a step 1406, an induced common voltage is measured as a function of time, over the measurement coil. At a step 1408, a first locator value is determined as a function of time by dividing the measured induced first voltage values with respective measured induced common voltage values. At a step 1410, the first locator values are mapped from time domain to a spatial domain. At a step 1412, the spatial domain first locator values are used for calculating a first velocity profile of the elongated magnetic probe. At a step 1414, the first velocity profile is used to determine the physiological parameter.

Figure 15:
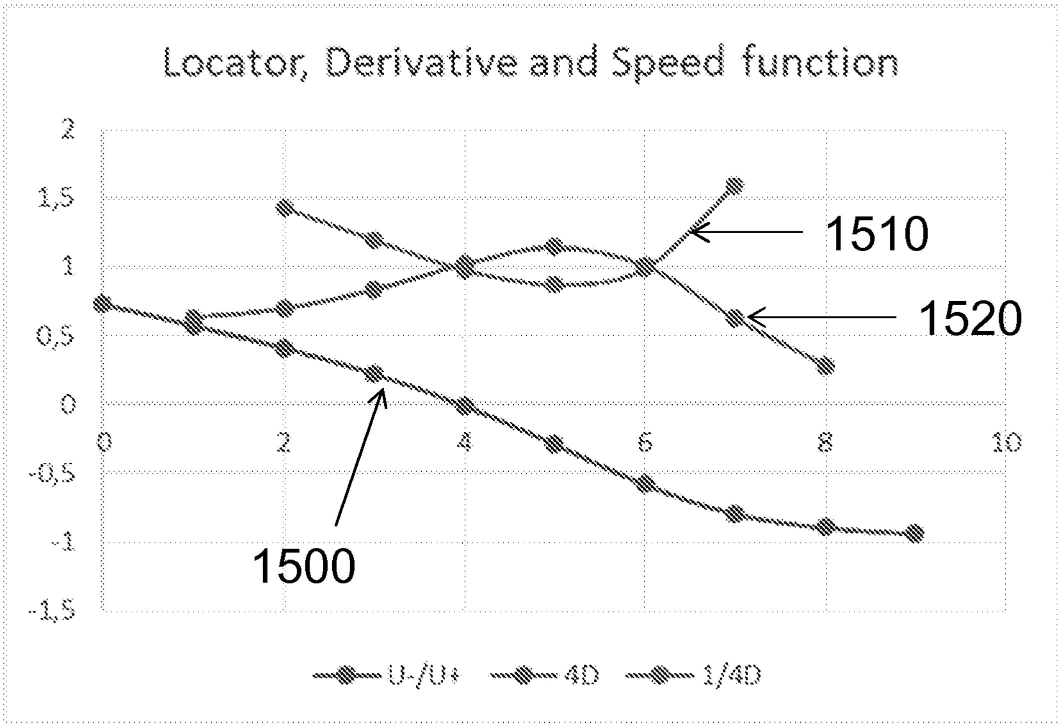
FIG. 15 is an illustration of determining velocity profile.

FIG. 15 is illustration of an measurement and calculated values as function fo probe movement (Z-axis in mm 0 to 10 mm). The locator 1500, is formed by taking the ratio of the U− and U+ signals shown in FIG. 12B. The derivative 1510 of the locator 1500 curve is formed dividing the increment of the points by the step length (1 mm). (The derivate curve 1510 is multiplied by −4, to make the FIG. 15 more easy to read). The inverse of the derivative curve 1520, is a first velocity profile as function of distance, in mm.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An apparatus for determining a physiological parameter, the apparatus comprising;

- an elongated magnetic probe having a first end, a second end opposite to the first end and a middle section between the first end and the second end;
- a driver coil arranged partially to surround the elongated magnetic probe;
- a measurement coil comprising at least a first section and a second section, and the measurement coil arranged partially to surround the elongated magnetic probe; and
- a controller configured to;
  - selectively energize the driver coil to create a magnetic force to initiate movement of the elongated magnetic probe to a direction of the first end;
  - measure first induced voltage values over the first section and induced voltage values over at least one of: the first section and the second section, or over the second section, as a function of time during a time of the movement of the elongated magnetic probe;
  - determine locator values as a function of time by dividing the first induced voltage values with the induced voltage values;
  - map the locator values as a function of time from the time domain to a spatial domain; and
  - calculate from the spatial domain locator values, a first velocity profile of the elongated magnetic probe, and use the calculated first velocity profile of the elongated magnetic probe to determine the physiological parameter.

2. The apparatus according to claim 1 wherein, when in use, the first section of the measurement coil surrounds a first section of the elongated magnetic probe and the second section of the measurement coil surrounds a second section of the elongated magnetic probe, wherein the first section of the elongated magnetic probe is different from the second section of the elongated magnetic probe, when the elongated magnetic probe is in its first spatial position.

3. The apparatus according to claim 2, wherein, when in use, the first section of the measurement coil does not surround the first section of the elongated magnetic probe and the second section of the measurement coil surrounds the second section of the elongated magnetic probe, when the elongated magnetic probe is in its second spatial position, which the second spatial position is different from the first spatial position.

4. The apparatus according to claim 1, wherein the time domain to spatial domain is mapped by at least one of: a pre-determined transfer function or a look up table.

5. The apparatus according to claim 1, wherein the first section and the second section of the measurement coil are connected in series.

6. The apparatus according to claim 1, wherein the measurement coil comprises a third section, the third section connected in series with the first and the second section of the measurement coil and the third section is arranged to surround a third section of the elongated magnetic probe.

7. The apparatus according to claim 1, wherein the induced voltage values are measured over all sections of the measurement coil.

8. The apparatus according to claim 1, wherein controller is further configured to

- measure second induced voltage values from a section other than the first section, as a function of time during a time of the movement of the elongated magnetic probe;
- determine a second locator values as function of time by dividing the second induced voltage values with the induced voltage values;
- map the second locator function from a time domain to a spatial domain;
- calculate from the spatial domain second locator values a second velocity profile of the elongated magnetic probe and
- use the calculated second velocity profile the elongated magnetic probe to update the physiological parameter.

9. The apparatus according to claim 8, wherein the second velocity profile comprises at least one of: a velocity in the spatial domain, a velocity in the time domain.

10. The apparatus according to claim 1, wherein the first velocity profile comprises at least one of: a velocity in the spatial domain, a velocity in the time domain.

11. The apparatus according to claim 1, wherein the apparatus is a tonometer.

12. A method for determining a physiological parameter, the method comprising:

- energizing a driver coil to move elongated magnetic probe to a direction of a first end of the elongated magnetic probe;
- measuring as a function of time, over a first section of a measurement coil, an induced first voltage;
- measuring as a function of time, over at least one of: a first section and a second section or over the second section of the measurement coil, an induced voltage;
- determining a first locator value as a function of time by dividing the measured induced first voltage with the induced voltage;
- mapping the first locator value from time domain to a spatial domain;
- calculating from the spatial domain first locator value a first velocity profile of the elongated magnetic probe; and using the first velocity profile to determine the physiological parameter.

13. The method according to claim 12, wherein the elongated magnetic probe is directed to move towards a patient to hit a surface of the patient body and bounce back thereof.

14. The method according to claim 12, wherein the measurements are carried out during the movement of the elongated magnetic probe to obtain induced voltage values as function of time.

15. The method according to claim 12, wherein the determination of the physiological parameter is carried out at least by one of: analysing acceleration of the elongated magnetic probe during its impact to the surface of the patient body, change of velocity before the impact and after the impact, amount of penetration of the elongated magnetic probe to the surface of the body.

16. The method according to claim 12, wherein the physiological parameter value is updated by measuring as a function of time, with a section of a measurement coil different from the first section, a second induced voltage;

determining a second locator values as function of time by dividing the second induced voltage with the induced voltage;

mapping the second locator function from a time domain to a spatial domain;

calculating from the spatial domain second locator values, a second velocity profile of the elongated magnetic probe as function of location;

using the calculated second velocity profile for updating the physiological parameter.

17. The method according to claim 16, wherein the second velocity profile comprises at least one of: the velocity in the spatial domain, the velocity in the time domain.

18. The method according to claim 12, wherein the first velocity profile comprises at least one of: a velocity in the spatial domain, a velocity in the time domain.

* * * * *